(12) United States Patent
Davis et al.

(10) Patent No.: US 7,503,227 B2
(45) Date of Patent: Mar. 17, 2009

(54) METHOD AND APPARATUS FOR MEASURING PARAMETERS OF A FLUID FLOW USING AN ARRAY OF SENSORS

(75) Inventors: Michael Davis, Glastonbury, CT (US); Timothy Bailey, Longmeadow, MA (US); Mark Fernald, Enfield, CT (US); Alan Kersey, South Glastonbury, CT (US); Christian O'Keefe, Durham, CT (US)

(73) Assignee: Cidra Corporate Services, Inc, Wallingford, CT (US)

( * ) Notice: Subject to any disclaimer, the term of this patent is extended or adjusted under 35 U.S.C. 154(b) by 14 days.

(21) Appl. No.: 11/487,184

(22) Filed: Jul. 13, 2006

(65) Prior Publication Data

US 2007/0044572 A1  Mar. 1, 2007

Related U.S. Application Data

(60) Provisional application No. 60/698,886, filed on Jul. 13, 2005.

(51) Int. Cl.
*G01F 1/34* (2006.01)
(52) U.S. Cl. .................................. 73/861.42
(58) Field of Classification Search ............... 73/61.79, 73/861.42, 61.47, 61.49, 152.18, 61.44, 861.04
See application file for complete search history.

(56) References Cited

U.S. PATENT DOCUMENTS

| | | | |
|---|---|---|---|
| 3,149,492 A | 9/1964 | Weinberg | |
| 4,048,853 A | 9/1977 | Smith et al. | |
| 4,080,837 A | 3/1978 | Alexander et al. | |
| 4,090,404 A | 5/1978 | Ligler et al. | |
| 4,144,768 A | 3/1979 | Anderson et al. | |
| 4,153,747 A | 5/1979 | Young et al. | |
| 4,216,403 A | 8/1980 | Krempl et al. | |
| 4,248,085 A | 2/1981 | Coulthard | |
| 4,361,937 A | 12/1982 | Davis | |
| 4,423,623 A | 1/1984 | Ho et al. | |
| 4,445,389 A | 5/1984 | Potzick et al. | |
| 4,454,767 A | 6/1984 | Shinkai et al. | |

(Continued)

FOREIGN PATENT DOCUMENTS

FR        2725787        4/1996

(Continued)

OTHER PUBLICATIONS

"Sonar-Based Volumetric Flow Meter for Pulp and Paper Applications" by Daniel L. Gysling and Douglas H. Loose—Dec. 3, 2002.

(Continued)

*Primary Examiner*—Jewel Thompson

(57) ABSTRACT

An apparatus for measuring velocity of a fluid passing through a pipe is provided. The apparatus includes a spatial array of sensors having at least two sensors disposed at different axial locations along the pipe, wherein the sensors provide at least one signal indicative of a stochastic parameter associated with a characteristic of the fluid, wherein the characteristic includes at least one of unsteady temperature, density, consistency, transparency, conductivity, capacitance, resistivity, and inductance. A signal processor is also provided, wherein the signal processor is configured to receive the at least one signal and determine the velocity of the fluid using the at least one signal.

23 Claims, 14 Drawing Sheets

U.S. PATENT DOCUMENTS

| | | | |
|---|---|---|---|
| 4,568,851 A | 2/1986 | Soni et al. | |
| 4,638,207 A | 1/1987 | Radice et al. | |
| 4,696,192 A * | 9/1987 | Yamashita et al. | 73/728 |
| 4,706,501 A | 11/1987 | Atkinson et al. | |
| 4,794,295 A | 12/1988 | Penneck et al. | |
| 4,849,946 A | 7/1989 | Beauducel | |
| 4,883,271 A | 11/1989 | French | |
| 4,896,540 A | 1/1990 | Shakkottai et al. | |
| 5,031,460 A | 7/1991 | Kanenobu et al. | |
| 5,040,415 A | 8/1991 | Barkhoudarian | |
| 5,083,452 A | 1/1992 | Hope | |
| 5,131,278 A | 7/1992 | Baumoel | |
| 5,218,197 A | 6/1993 | Carroll | |
| 5,285,675 A | 2/1994 | Colgate et al. | |
| 5,367,911 A | 11/1994 | Jewell et al. | |
| 5,398,542 A | 3/1995 | Vasbinder | |
| 5,524,475 A | 6/1996 | Kolpak et al. | |
| 5,526,844 A | 6/1996 | Kamen et al. | |
| 5,550,791 A | 8/1996 | Peloquin | |
| 5,591,922 A | 1/1997 | Segeral et al. | |
| 5,661,237 A * | 8/1997 | Dussan V. et al. | 73/152.18 |
| 5,670,720 A | 9/1997 | Clark et al. | |
| 5,741,980 A | 4/1998 | Hill et al. | |
| 5,770,805 A | 6/1998 | Castel | |
| 5,770,806 A | 6/1998 | Hiismaki | |
| 5,835,884 A | 11/1998 | Brown | |
| 5,845,033 A | 12/1998 | Berthold et al. | |
| 5,948,959 A | 9/1999 | Peloquin | |
| 6,016,702 A | 1/2000 | Maron | |
| 6,135,209 A | 10/2000 | Uhlenkott | |
| 6,148,672 A | 11/2000 | Cawley et al. | |
| 6,151,958 A | 11/2000 | Letton et al. | |
| 6,202,494 B1 | 3/2001 | Ricbel et al. | |
| 6,271,621 B1 | 8/2001 | Ito et al. | |
| 6,349,599 B1 | 2/2002 | Lynnworth et al. | |
| 6,354,147 B1 | 3/2002 | Gysling et al. | |
| 6,378,357 B1 | 4/2002 | Han et al. | |
| 6,397,683 B1 | 6/2002 | Hagenmeyer et al. | |
| 6,435,030 B1 | 8/2002 | Gysling et al. | |
| 6,443,226 B1 | 9/2002 | Diener et al. | |
| 6,450,037 B1 | 9/2002 | McGuinn et al. | |
| 6,463,813 B1 | 10/2002 | Gysling | |
| 6,526,834 B1 | 3/2003 | Kohler et al. | |
| 6,536,291 B1 | 3/2003 | Gysling | |
| 6,550,342 B2 | 4/2003 | Croteau et al. | |
| 6,558,036 B2 | 5/2003 | Gysling et al. | |
| 6,587,798 B2 | 7/2003 | Kersey et al. | |
| 6,601,458 B1 | 8/2003 | Gysling et al. | |
| 6,609,069 B2 | 8/2003 | Gysling | |
| 6,644,130 B2 | 11/2003 | Imai et al. | |
| 6,668,664 B1 | 12/2003 | Ohkawa | |
| 6,691,584 B2 | 2/2004 | Gysling et al. | |
| 6,698,297 B2 | 3/2004 | Gysling | |
| 6,732,575 B2 | 5/2004 | Gysling et al. | |
| 6,782,150 B2 | 8/2004 | Davis et al. | |
| 6,813,962 B2 | 11/2004 | Gysling et al. | |
| 6,837,098 B2 | 1/2005 | Gysling et al. | |
| 6,862,920 B2 | 3/2005 | Gysling et al. | |
| 6,868,737 B2 | 3/2005 | Croteau et al. | |
| 6,889,562 B2 | 5/2005 | Gysling et al. | |
| 6,898,541 B2 | 5/2005 | Gysling et al. | |
| 6,935,189 B2 * | 8/2005 | Richards | 73/861.04 |
| 6,945,095 B2 | 9/2005 | Johansen | |
| 7,000,485 B2 | 2/2006 | Ao et al. | |
| 7,165,454 B2 * | 1/2007 | Hayashi et al. | 73/649 |
| 7,165,464 B2 * | 1/2007 | Gysling et al. | 73/861.42 |
| 7,330,797 B2 * | 2/2008 | Bailey et al. | 702/50 |
| 2002/0123862 A1 | 9/2002 | Gysling et al. | |
| 2002/0129662 A1 | 9/2002 | Gysling et al. | |
| 2003/0010126 A1 | 1/2003 | Romanet et al. | |
| 2003/0038231 A1 | 2/2003 | Davis et al. | |
| 2003/0089161 A1 | 5/2003 | Gysling | |
| 2003/0136186 A1 | 7/2003 | Gysling et al. | |
| 2003/0154036 A1 | 8/2003 | Gysling et al. | |
| 2004/0016284 A1 | 1/2004 | Gysling et al. | |
| 2004/0069069 A1 | 4/2004 | Croteau et al. | |
| 2004/0074312 A1 | 4/2004 | Gysling | |
| 2004/0144182 A1 | 7/2004 | Gysling et al. | |
| 2004/0167735 A1 | 8/2004 | Rothman et al. | |
| 2004/0168522 A1 | 9/2004 | Fernald et al. | |
| 2004/0168523 A1 | 9/2004 | Bailey et al. | |
| 2004/0199340 A1 | 10/2004 | Kersey et al. | |
| 2004/0210404 A1 | 10/2004 | Gysling et al. | |
| 2004/0226386 A1 | 11/2004 | Gysling et al. | |
| 2004/0231431 A1 | 11/2004 | Sullivan et al. | |
| 2004/0255695 A1 | 12/2004 | Gysling et al. | |
| 2005/0005711 A1 | 1/2005 | Gysling | |
| 2005/0005713 A1 | 1/2005 | Winston et al. | |
| 2005/0011283 A1 | 1/2005 | Gysling et al. | |
| 2005/0011284 A1 | 1/2005 | Gysling et al. | |

FOREIGN PATENT DOCUMENTS

| | | |
|---|---|---|
| GB | 2282931 | 4/1995 |
| WO | WO 03/062759 | 7/2003 |
| WO | WO 0068080 | 8/2004 |

OTHER PUBLICATIONS

"Sonar-Based Volumetric Flow Meter for Chemical and Petrochemical Applications" by Daniel L. Gysling and Douglas H. Loose—Dec. 14, 2003.

"Noise and Vibration Control Engineering Principles and Applications" Leo L. Beranek and Istvan L. Ver, A. Wiley Interscience Publication, pp. 537-541, Aug. 1992.

"Two Decades of Array Signal Processing Research, The Parametric Approach", H. Krim and M. Viberg, IEEE Signal Processing Mazazine, Jul. 1996, pp. 67-94.

Development of an Array of Pressure Sensors with PVDF film, Experiments in Fluids 26, Jan. 8, 1999, Springer-Verlag, pp. 27-35.

"Vicous Attentuation of Acoustic Waves in Suspension" by R.L. Givson, Jr. and M.N. Toksoz, Acoustic Society of America, May 1898 pp. 1925-1933.

"New Flowmeter Principle" by Walt Boyes—Published in Flow Control Magazine—Oct. 2003 Issue.

"Piezoelectric Polymers" By J.S. Harrison and Z. Qunaies—ICASE Report pp. 1-26.

"Mass Fraction Measurements In Multiphase Flow Using a Clamp on PVDF Array" Johan Carlson, Oct. 2000.

"PVDF and Array Transducers" Robert A. Day, NDTnet- Sep. 1996, vol. 1. No. 9.

"Polymer Piezoelectric Transducers for Ultrasonic NDE", Yhoseph Bar-Chohen, Tianji Xu and Shyh-Shiuh Lih, NDTnet—Sep. 1996, vol. 1, No. 9.

"Piezofilm Sensors Technical Manual"—Measurements Specialities, Inc. P/N 1005663-1—Rev. B Apr. 2, 1999.

* cited by examiner

METHOD AND APPARATUS FOR MEASURING PARAMETERS OF A FLUID FLOW USING AN ARRAY OF SENSORS

RELATED APPLICATIONS

This application claims the benefit of U.S. Provisional Patent Application No. 60/698,886, filed Jul. 13, 2005, the contents of which are incorporated by reference herein in its entirety.

FIELD OF THE INVENTION

The present disclosure relates generally to a method and apparatus for measuring parameters of a fluid flow, and more particularly to a method and apparatus for measuring parameters of a fluid flow using an array of sensors.

BACKGROUND OF THE INVENTION

A fluid flow process, or flow process, typically includes any process that involves the flow of a fluid through pipes, ducts, or other conduits, as well as through fluid control devices such as pumps, valves, orifices, heat exchangers, and the like. Flow processes are found in many different types of industries such as the oil and gas industry, refining, food and beverage industry, chemical and petrochemical industry, pulp and paper industry, power generation, pharmaceutical industry, and water and wastewater treatment industry. Additionally, the flow process may involve many different types of fluids, such as single phase fluids (e.g., gas, liquid or liquid/liquid mixture) and/or multi-phase mixtures (e.g. paper and pulp slurries or other solid/liquid mixtures), wherein the multi-phase mixture may be a two-phase liquid/gas mixture, a solid/gas mixture or a solid/liquid mixture, gas entrained liquid or a three-phase mixture. Currently, a variety of sensing technologies exist for measuring various physical parameters of the fluids in an industrial flow process, wherein the physical parameters may include, for example, volumetric flow rate, composition, consistency, density, and mass flow rate.

One such sensing technology is described in commonly-owned U.S. Pat. No. 6,609,069 to Gysling, entitled "Method and Apparatus for Determining the Flow Velocity Within a Pipe" (hereinafter "'069 patent"), which is incorporated herein by reference in its entirety. The '069 patent describes a method and corresponding apparatus for measuring the flow velocity of a fluid flowing within an elongated body, such as a pipe, by sensing vortical disturbances convecting with the fluid. The method as disclosed in the '069 patent includes providing an array of at least two sensors disposed at predetermined locations along the elongated body, wherein each sensor is for sampling the pressure of the fluid at the position of the sensor at a predetermined sampling rate. The method also includes accumulating the sampled data from each sensor at each of a number of instants of time spanning a predetermined sampling duration and constructing from the accumulated sampled data at least a portion of a so called k-ω plot, where the k-ω plot is indicative of a dispersion relation for the propagation of acoustic pressures emanating from the vortical disturbances. Furthermore, the method includes identifying a convective ridge in the k-ω plot, determining the orientation of the convective ridge in the k-ω plot and determining the flow velocity based on a predetermined correlation of the flow velocity with the slope of the convective ridge of the k-ω plot.

Another such sensing technology is described in commonly-owned U.S. Pat. No. 6,354,147 (hereinafter "'147 patent") and U.S. Pat. No. 6,732,575 (hereinafter "'575 patent") to Gysling et. al, both of which are incorporated by reference herein in their entireties. Both the '167 patent and the '575 patent describe a spatial array of acoustic pressure sensors placed at predetermined axial locations along a pipe. The pressure sensors provide acoustic pressure signals to signal processing logic which determines the speed of sound of the fluid (or mixture) in the pipe using any of a number of acoustic spatial array signal processing techniques with the direction of propagation of the acoustic signals along the longitudinal axis of the pipe. The speed of sound is provided to logic, which calculates the percent composition of the mixture, e.g., water fraction, or any other parameter of the mixture, or fluid, that is related to the sound speed, wherein the logic may also determine the Mach number of the fluid.

SUMMARY OF THE INVENTION

An apparatus for measuring velocity of a fluid passing through a pipe is provided. The apparatus includes a spatial array of sensors having at least two sensors disposed at different axial locations along the pipe, wherein the sensors provide at least one signal indicative of a stochastic parameter associated with a characteristic of the fluid, wherein the characteristic includes at least one of unsteady temperature, density, consistency, transparency, conductivity, capacitance, resistivity, and inductance. A signal processor is also provided, wherein the signal processor is configured to receive the at least one signal and determine the velocity of the fluid using the at least one signal.

Furthermore, a method for measuring velocity of a fluid passing through a pipe is provided and includes generating at least one signal indicative of a stochastic parameter associated with the fluid, wherein the stochastic parameter includes at least one of unsteady temperature, density, consistency, transparency, conductivity, capacitance, resistivity, and inductance. The method also includes determining a velocity of the fluid responsive to the at least one signal.

Furthermore, an apparatus for measuring velocity of a fluid passing through a pipe is provided, wherein the apparatus includes at least two sensors disposed at different axial locations along the pipe, wherein the at least two sensors provide at least one signal indicative of a stochastic parameter associated with a characteristic of the fluid and include at least one of a magmeter sensor and a consistency meter sensor, the at least two sensors being configurable for operation in at least one of a first mode and a second mode. The apparatus also includes a signal processor, wherein the signal processor is configured to receive the at least one signal and determine the velocity of the fluid using the at least one signal.

BRIEF DESCRIPTION OF THE DRAWINGS

Referring now to the drawings, the foregoing and other features and advantages of the present invention will be more fully understood from the following detailed description of illustrative embodiments, taken in conjunction with the accompanying drawings in which like elements are numbered alike.

DETAILED DESCRIPTION

As is known, U.S. patent application Ser. Nos. 10/007,749, 10/349,716 and 10/376,427, all of which are incorporated by reference herein in their entireties, describe how various parameters of a fluid (e.g., velocity, volumetric flow rate, speed of sound, and composition) can be determined by applying array processing techniques to measurements of unsteady pressures within the fluid flow. These unsteady pressures may be caused by one or both of acoustic waves propagating through the fluid within the pipe and/or pressure disturbances that convect with the fluid flowing within the pipe (e.g., turbulent eddies and vortical disturbances). This methodology has been demonstrated using arrays of various transducers, including a variety of pressure and strain based measurement devices. For example, these sensors may include piezoelectric sensors, piezoresistive sensors, strain gauges, PVDF sensors, optical sensors, ported ac pressure sensors, accelerometers, velocity sensors and displacement sensors, among others. While these sensors tend to work well, it is contemplated that other types of sensor may be used as well. For example, as will be discussed further hereinafter, it is contemplated that these unsteady pressures may be sensed using microphones. It is further contemplated that stochastic parameters other than unsteady pressures may be sensed by the array of sensors and used to determine the parameters of the fluid. For example, an array of sensors may sense unsteady temperature, density, consistency, transparency, conductivity, resistivity, capacitance, inductance, and the like. Accordingly, each sensor may include any type of sensor capable of measuring a stochastic parameter of the fluid.

Figure 1:
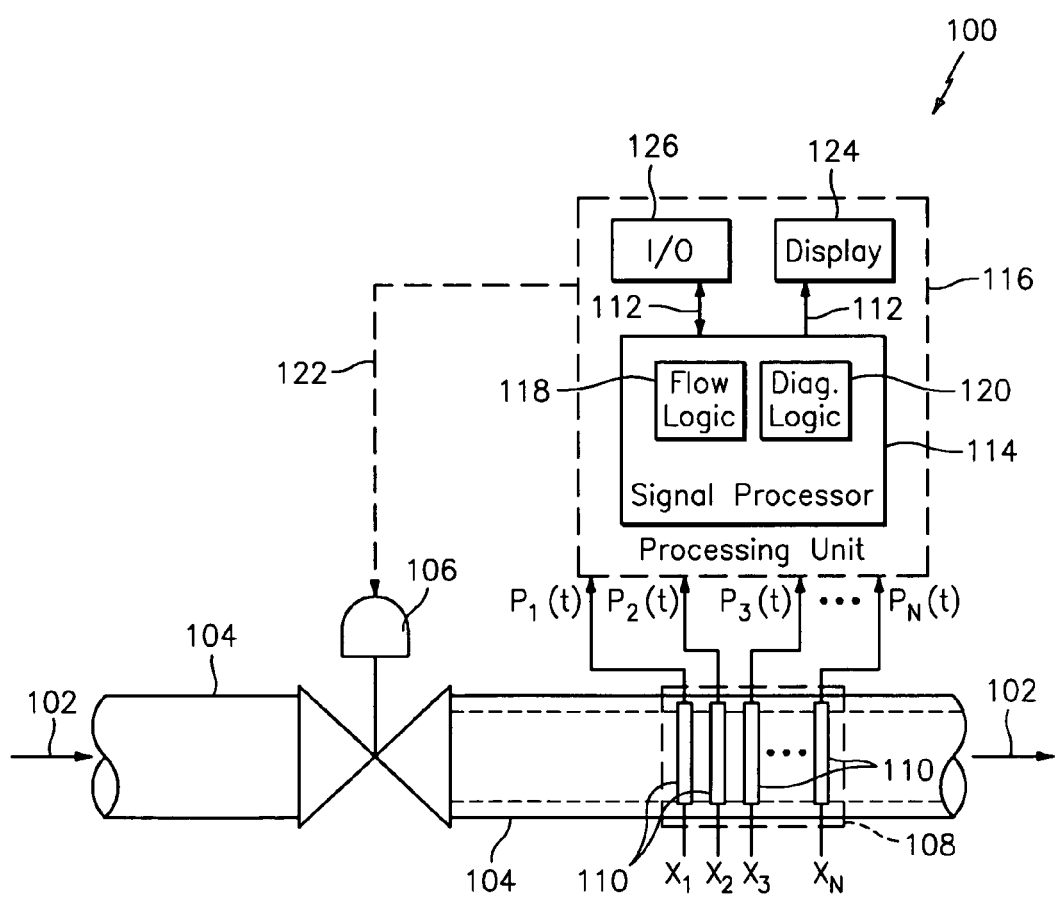
FIG. 1 is a schematic diagram of an apparatus for determining at least one parameter associated with a fluid flowing in a pipe.

Referring to FIG. 1, an apparatus 100 for measuring at least one parameter associated with a fluid 102 flowing within a pipe 104 is shown, wherein the parameter associated with the fluid 102 may include, but is not limited to, for example, at least one of: velocity of the fluid 102, density of the fluid 102, volumetric flow rate of the fluid 102, mass flow rate of the fluid 102, composition of the fluid 102, entrained air in the fluid 102, consistency of the fluid 102, size of particles in the fluid 102, and the health of a device 106 in fluid communication with the pipe 104. Furthermore, it should be appreciated that the fluid 102 may be a single or multiphase fluid 102 flowing through a duct, conduit or other form of pipe 104.

The apparatus 100 may include a spatial array 108 of at least two sensors 110 disposed at different axial locations $x_1$ ... $x_N$ along the pipe 104. Each of the sensors 110 may provide a signal P(t) indicative of a stochastic parameter of the fluid 102 within the pipe 104 at a corresponding axial location $x_1$ ... $x_N$ of the pipe 104. The stochastic parameter may include, but not be limited to, one or more of: unsteady temperature, pressure, density, consistency, transparency, conductivity, capacitance, resistivity, inductance, and the like. In one embodiment, each sensor 110 may include a microphone, while in other embodiments each sensor 110 may include sensors commonly associated with magnetic flow meters (magmeters), temperature sensors, densitometers, consistency meters, light meters, conductivity meters, capacitance meters, inductance meters, or the like. A signal processor 114 may receive the signals $P_1(t) \ldots P_N(t)$ from the sensors 110 in the array 108, determine the parameter of the fluid 102 using signals from the sensors 110 and output the parameter as a signal 112.

It should be appreciated that while the apparatus 100 is shown as including four sensors 110, it is contemplated that the array 108 of sensors 110 may include two or more sensors 110, each providing a signal P(t) indicative of a characteristic associated with the fluid 102 within the pipe 104 at a corresponding axial location X of the pipe 104. For example, the apparatus 100 may include 2, 3, 4, 5, 6, 7, 8, 9, 10, 11, 12, 13, 14, 15, 16, 17, 18, 19, 20, 21, 22, 23, or 24 sensors 110. Generally, the accuracy of the measurement improves as the number of sensors 110 in the array 108 increases. It should be further appreciated that the degree of accuracy provided by the greater number of sensors 110 is offset by the increase in complexity and time for computing the desired output parameter of the flow 102. Therefore, the number of sensors 110 used is dependent at least on the degree of accuracy desired and the desired update rate of the output parameter provided by the apparatus 100.

The signals $P_1(t) \ldots P_N(t)$ provided by the sensors 110 in the array 108 are processed by the signal processor 114, which may be part of a larger processing unit 116. For example, the signal processor 114 may be a microprocessor and the processing unit 116 may be a personal computer or other general purpose computer. It should also be appreciated that the signal processor 114 may be any one or more signal processing devices for executing programmed instructions, such as one or more microprocessors or application specific integrated circuits (ASICS), and may include memory for storing programmed instructions, set points, parameters, and for buffering or otherwise storing data.

The signal processor 114 may determine the one or more parameters 112 of the fluid 102 by applying the data from the sensors 110 to flow logic 118 that may be executed by signal processor 114, wherein the flow logic 118 is described in further detail hereinafter. The one or more parameters 112 may include, but not be limited to, such parameters as velocity, volumetric flow rate, mass flow rate, density, composition, entrained air, consistency, particle size, velocity, mach number, speed of sound propagating through the fluid 102, and/or other parameters of the fluid 102.

The signal processor 114 may also apply one or more of the signals from sensors 110 and/or one or more parameters 112 from the flow logic 118 to diagnostic logic 120, wherein diagnostic logic 120 is described in further detail hereinafter. The diagnostic logic 120 may be executed by the signal processor 114 to diagnose the health of any device 106 in the process flow that may cause changes in the characteristic sensed by the sensors 110. Referring back to FIG. 1, although device 106 is depicted as a valve, it is contemplated that device 106 may be any machinery, component, or equipment, e.g., motor, fan, pump, generator, engine, gearbox, belt, drive, pulley, hanger, clamp, actuator, valve, meter, or the like suitable to the desired end purpose. It should be appreciated that the signal processor 114 may output one or more parameters 112 indicative of the health of the device 106. Furthermore, the signal processor 114 may also output a control signal 122 to control the device 106 in response to parameter 112.

The signal processor 114 may output the one or more parameters 112 to a display 124 or another input/output (I/O) device 126, wherein the I/O device 126 may also accept user input parameters 128 as may be necessary for the flow logic 118 and/or diagnostic logic 120. Additionally, the I/O device 126, display 124, and signal processor 114 unit may be mounted in a common housing, which may be attached to the array 108 by a flexible cable, wireless connection, or the like, wherein the flexible cable may also be used to provide operating power from the processing unit 116 to the array 108 if necessary.

Figure 2:
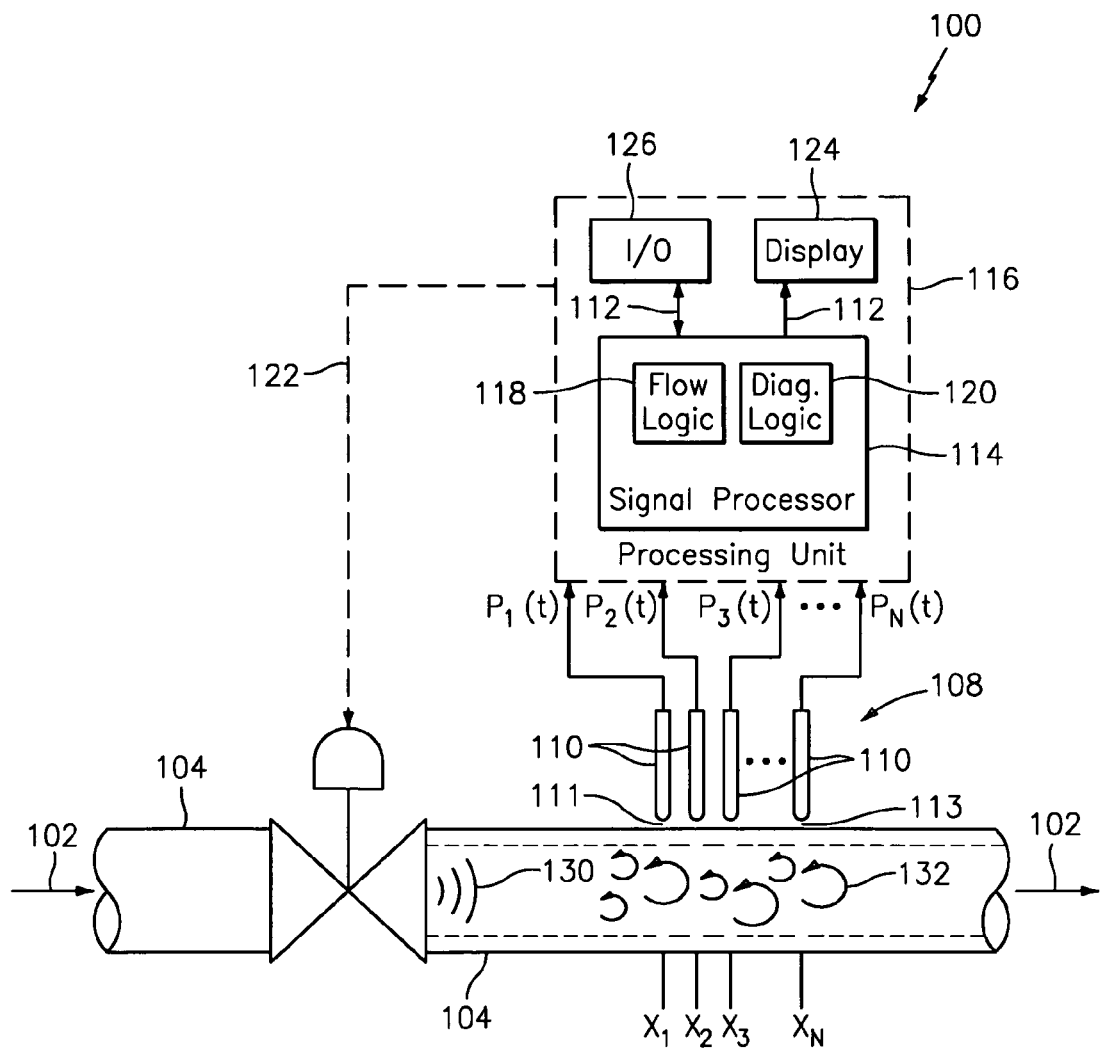
FIG. 2 is a schematic diagram of an apparatus for determining at least one parameter associated with a fluid flowing in a pipe using an array of microphones.

As previously noted, U.S. patent application Ser. Nos. 10/007,749, 10/349,716, and 10/376,427 describe that various parameters of a fluid (e.g., velocity and volumetric flow rate) can be determined using the measurement of unsteady pressure fluctuations in a fluid flow using array processing techniques. This flow methodology has been demonstrated using a variety of transducers, including various pressure and strain measurement devices. Referring to FIG. 2, it is contemplated that rather than using strain measurement devices as the sensors 110, each of the sensors 110 may include a microphone disposed proximate an outer surface of the pipe 104. In this embodiment, each microphone 110 senses unsteady pressures within the pipe 104, as may be caused by one or both of acoustic waves 130 propagating through the fluid 102 within the pipe 104 and/or pressure disturbances 132 that convect with the fluid 102 flowing in the pipe 104 (e.g., turbulent eddies and vortical disturbances), at a corresponding axial position X by sensing the acoustics (e.g., sound pressure level, acoustic signature, etc.) generated in a fluid 111 disposed between the microphone 110 and an outer surface of the pipe 104. The sensors (microphones) 110 output a signal $P_1(t) \ldots P_N(t)$ indicative of the acoustics, and provides the signal to the signal processor 114, which applies these signals to the flow logic 118 and/or diagnostic logic 120.

The fluid 111 (e.g., air) may be disposed in a cavity 113 formed between the microphones 110 and the pipe 104 wall, and the microphones 110 may be clamped to the outside of the pipe 104. Because signal energy is transferred by the fluid 111 between the microphone 110 and the wall of the pipe 104, the sensors 110 should be relatively immune to pipe vibration in comparison to a sensor 110 in direct contact with the pipe wall. Testing of this design suggests that there is a good correlation between the internal unsteady pressures in the pipe 104 and the microphone 110 signal. One suitable microphone 110 may be commercially available as model 377A25 from PCB Piezotronics, Inc. of Depew, N.Y. and another suitable microphone may be model number 130D21 from PCB Piezotronics, Inc.

In another aspect, it is contemplated that stochastic parameters other than unsteady pressures in the fluid 102 may be sensed by the array 108. Stochastic parameters of a moving fluid vary over time and move (convect) either at the same velocity as the fluid or at a velocity that can be correlated to the velocity of the fluid 102. As will be described in further detail hereinafter, as the stochastic parameter convects with the fluid 102 past the array 108, array processing can be performed by exploiting what is sometimes called the dispersion relationship associated with convecting stochastic parameters.

Figure 3:
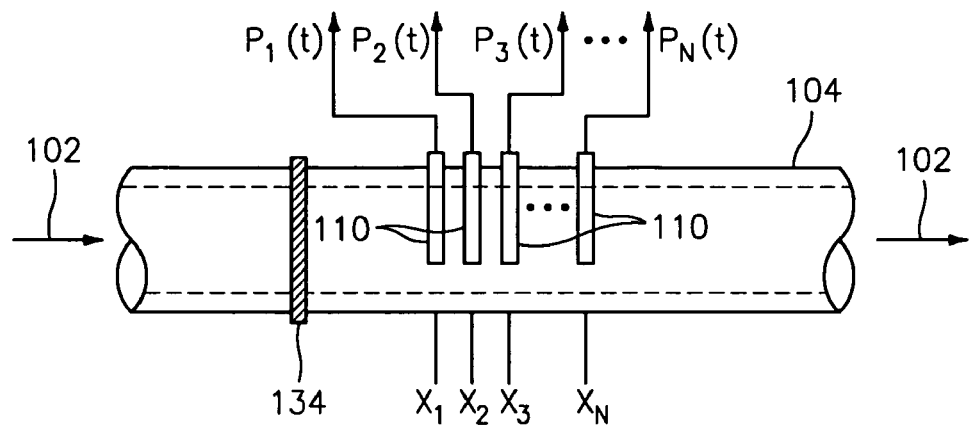
FIG. 3 is a schematic diagram of an apparatus for determining at least one parameter associated with a fluid flowing in a pipe using an array of temperature sensors.
Figure 4:
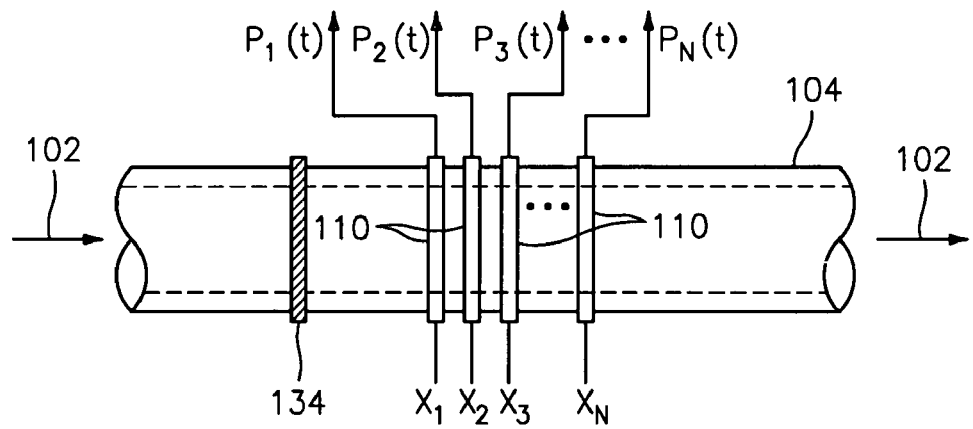
FIG. 4 is a schematic diagram of an apparatus for determining at least one parameter associated with a fluid flowing in a pipe using an array of strain-based sensors to measure strain induced on the pipe surface by unsteady fluid temperature.

Referring to FIG. 3 and FIG. 4, one example of a stochastic parameter that may be sensed by the array 108 is temperature. More specifically, many fluids 102 flowing through the pipe 104 will exhibit small temperature variations along the fluid 102. These temperature variations tend to convect or "ride" along with the fluid flow and therefore represent a characteristic that is directly tied to the flow rate of the fluid 102. Any tracking of the temperature propagation can then be applied by the signal processor 114 (FIG. 1) to the flow logic 118 to measure the fluid 102 velocity using array processing algorithms, as described in further detail hereinafter under the heading "velocity measurement".

In the embodiment of FIG. 3, each of the sensors 110 comprises a temperature sensor located within the pipe 104. The sensors 110 are used to map the temperature fluctuations and provide data to enable the measurement. The sensors 110 output a signal $P_1(t) \ldots P_N(t)$ indicative of the temperature at a corresponding axial location X. The signal processor 19 (FIG. 1) applies these signals to the flow logic 118 (FIG. 1) to determine the velocity and other parameters of the fluid 102. It should be appreciated that where the fluid 102 flowing through the pipe 104 does not inherently have enough temperature fluctuations to produce a measurable signal, a heat source or heat sink 134 can be used to generate the temperature variations. In the embodiment of FIG. 4, the effect of the temperature variations on the pipe 104 is measured. For example, an array of strain-based sensors 110 may be used to measure the surface strain induced on the pipe 104 surface by the temperature fluctuations. Each sensor 110 outputs a signal indicative of the pipe surface strain, which is indicative of temperature variation, at a corresponding axial location X. Alternatively, the temperature on the outer pipe wall may be measured directly. The signal processor 114 (FIG. 1) applies these signals to the flow logic 118 to determine the velocity and other parameters of the fluid 102. It should be appreciated that for a given temperature change $\Delta t$, the strain induced, $\epsilon$, will be given by:

$$\epsilon = \alpha^* \Delta t, \quad \text{(Eqn. 1)}$$

where $\alpha$ is the coefficient of linear expansion. For example, consider typical steel which has a coefficient of linear expansion α of 12×10⁻⁶/° C. Therefore, a temperature change of 0.1° C. will induce 1.2 microstrains onto the steel.

As described in U.S. patent application Ser. Nos. 10/349,716 and 10/376,427, strain fluctuations on the pipe 104 surface are to be measured, wherein each of the sensors 110 may include a piezoelectric film sensor. The piezoelectric film sensors may include a piezoelectric material or film to generate an electrical signal proportional to the degree that the pipe 104 material is mechanically deformed or stressed. The piezoelectric sensing element is typically conformed to allow complete or nearly complete circumferential measurement of induced strain to provide a circumferential-averaged signal. The sensors 110 can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 104 due to temperature variations within the fluid 102. Strain within the pipe 104 is transduced to an output voltage or current by the attached piezoelectric sensor. The piezoelectrical material or film may be formed of a polymer, such as polarized fluoropolymer, polyvinylidene fluoride (PVDF). The piezoelectric film sensors may be similar to that as described in U.S. patent application Ser. Nos. 10/712,818, 10/712,833, and 10/795,111, each of which are incorporated herein by reference in their entireties.

With the aforementioned PVDF sensors, for example, a strain of 10 picostrain can be seen, giving a corresponding temperature change resolution of 8×10⁻⁷° C. With this type of resolution, very small changes in temperature can be seen in the fluid 102 flowing through the pipe 104. This indicates that many fluids will have enough fluctuations that can be measured using this technique. In situations where the fluid 102 flowing through the pipe 104 does not inherently have enough temperature fluctuations to produce a measurable signal, a heat source or heat sink 134 can be used to generate the temperature variations.

Figure 6:
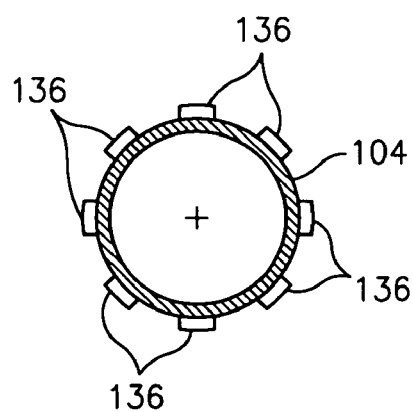
FIG. 6 is an embodiment of FIG. 5 where multiple electrodes are placed around the circumference of the pipe.
Figure 5:
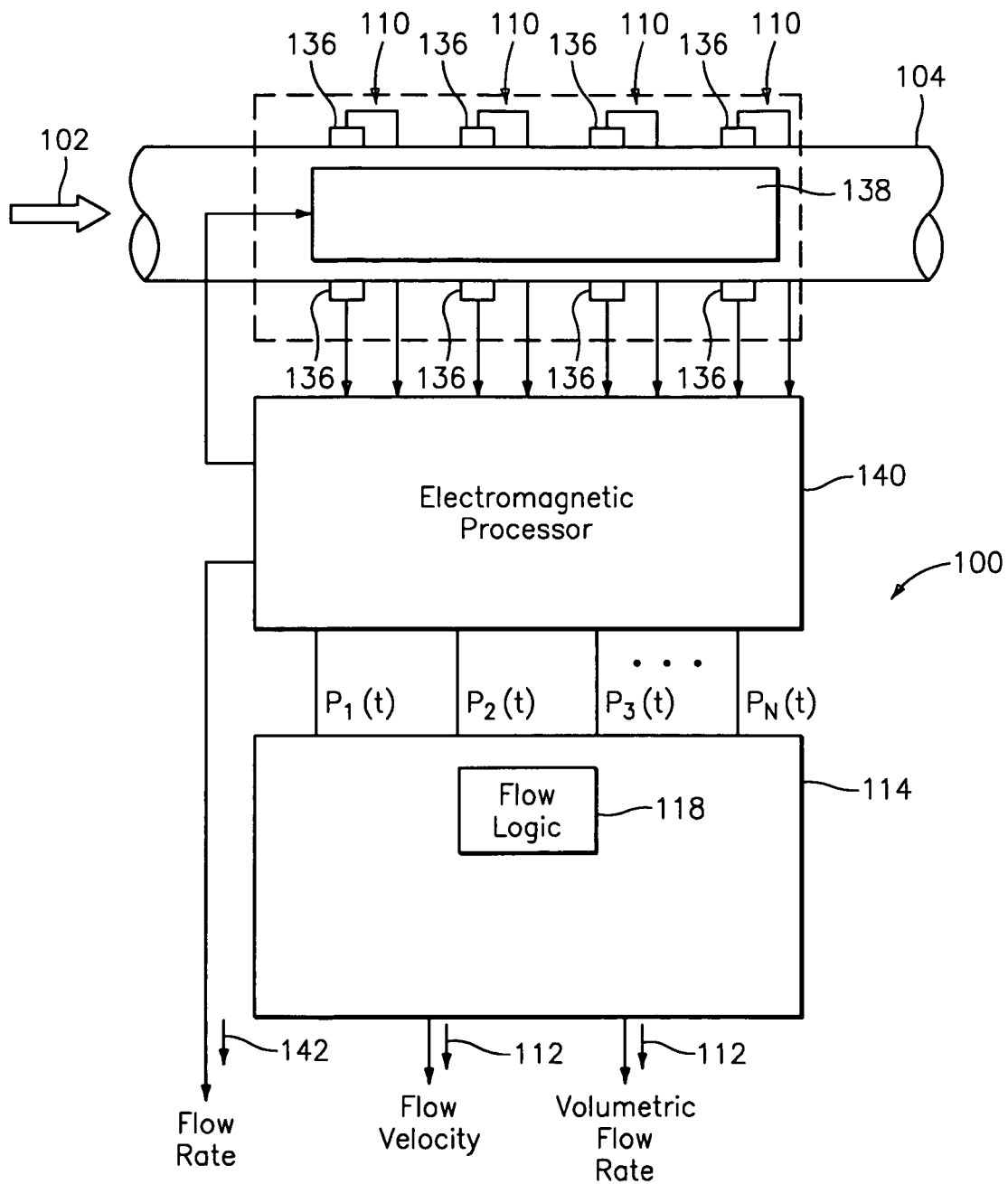
FIG. 5 is a schematic diagram of an apparatus for determining at least one parameter associated with a fluid flowing in a pipe using an array of sensors that detect voltage across the fluid flowing through a magnetic field.
Figure 7:
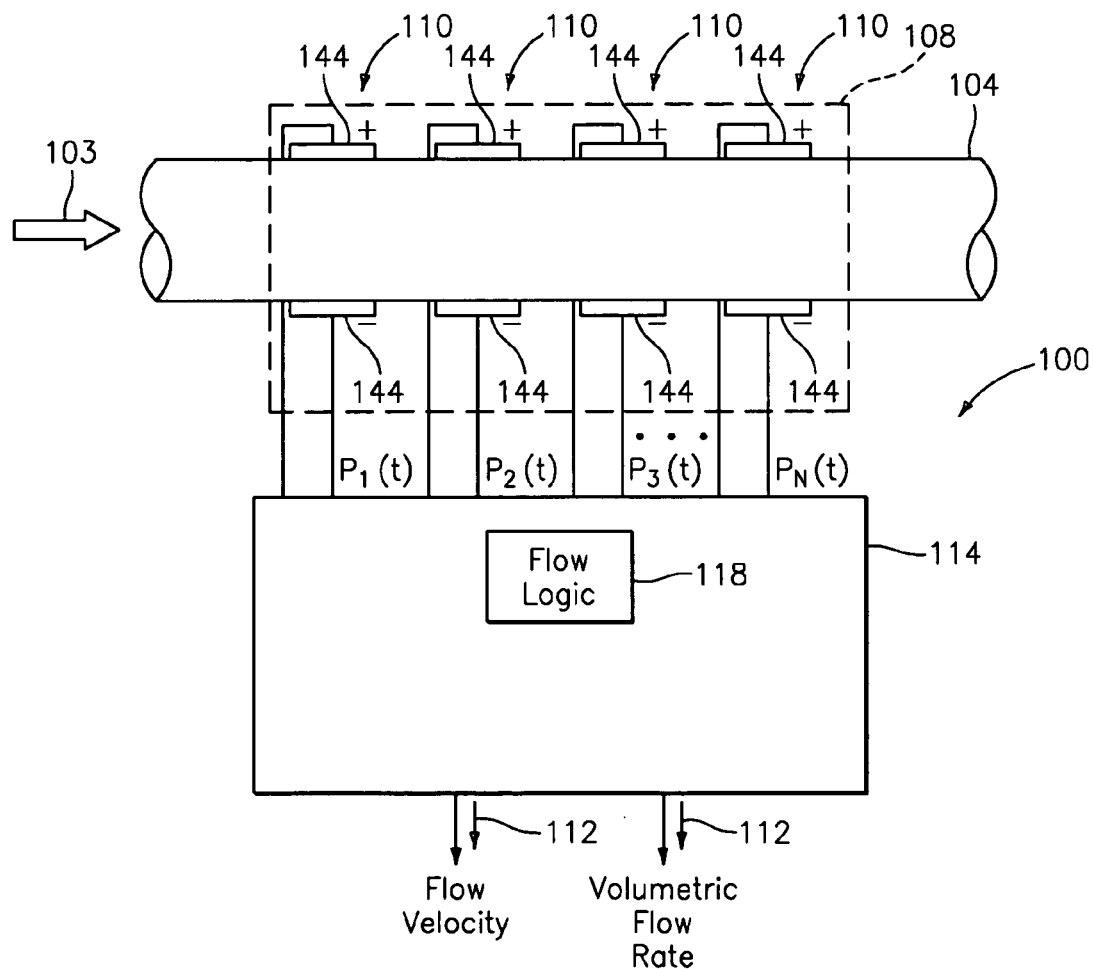
FIG. 7 is a schematic diagram of an apparatus for determining at least one parameter associated with a fluid flowing in a pipe using an array of sensors that provide a signal indicative of an electrical characteristic of the fluid.

Referring to FIG. 5, FIG. 6, and FIG. 7, other examples of stochastic parameters that may be sensed by the array 108 include those which may affect various electrical and magnetic parameters. For example, it is known that flow velocity may be obtained by measuring the changes in voltage induced in a conductive fluid passing across a controlled magnetic field. Commercially available magnetic flow meters (magmeters, electromagnetic flowmeters, or induction meters) use this principle measure the flow rate of the fluid.

A typical magnetic flowmeter (i.e., magmeter) includes electric coils disposed around or near the pipe and a pair of electrodes arranged diametrically across the pipe or at the tip of a probe inserted into the pipe. If the fluid is electrically conductive, its passing through the pipe is equivalent to a conductor passing through the magnetic field, which induces changes in voltage across the electrodes. The higher the flow speed, the higher the voltage. A signal processor within the magnetic flowmeter uses the voltage signal from the pair of electrodes to determine the fluid flow rate based on the cross sectional area of the pipe 104. Problematically, however, turbulent flows and multi-phase flows can cause instabilities and problems with magnetic flowmeters such as increased fluctuations in the signal output by the electrodes. These fluctuations are seen as noise, which tend to result in degraded performance of the magnetic flowmeter.

In the embodiment of FIG. 5, each sensor 110 in the array 108 comprises a pair of electrodes 136 which detects voltage across a fluid 102 flowing through a magnetic field. The magnetic field may be generated by coils 138 positioned proximate the pipe 104 at different axial locations X along the length of the pipe 104. For single phase fluids, signals from each pair of electrodes 136 in the array 108 can be averaged and used as input to a standard magnetic flowmeter processor 140, which determines a flow rate of the fluid 102 using the averaged signals and provides an output signal 142 indicative of the flow rate. For multi-phase flow, turbulent flow, and/or when the noise on the individual electrode pairs exceed a certain level, the voltage signals $P_1(t) \ldots P_N(t)$ from each electrode pair is provided to the signal processor 114, which applies these signals to the flow logic 118 to determine the velocity and other parameters of the fluid 102. In this mode, the array 108 detects disturbances due to turbulence, density changes, or other coherent features convecting with the fluid 102 flow past the array 108. In other words, what would be considered "noise" for a typical magnetic flowmeter is tracked across the array 108 of electrodes 136 using phased array processing, such as sonar processing to determine the velocity of the fluid flow.

The present invention contemplates a standard magmeter having two or more magnetic sensors disposed a different locations X along the length of the pipe 104, as described hereinbefore. The magmeter would include additional processing to perform the array processing of the sensor data as described herein to provide a velocity and volumetric flow of the fluid 102 flowing within the pipe 104. It is further contemplated that this embodiment may function in two modes. For example, the invention may operate in a first mode that functions as a standard magmeter and/or the magmeter may then be switched to a second mode that functions as the array-based meter (described herein) when the noise on the electrodes of a sensor 110 exceeds a certain level. FIG. 6 depicts an embodiment which may be useful for situations where the flow is stratified and may include multiple electrodes 136 placed around the circumference of the pipe 104. In this embodiment, the electrodes 136 can be used to detect different velocity components due to the turbulence and/or density changes in the fluid flowing through different parts of the pipe 104.

FIG. 7 depicts an embodiment in which each sensor 110 in the array 108 includes a pair of electrodes 144 positioned across the fluid 102, wherein each pair of electrodes 144 provides a signal indicative of the capacitance of the fluid 102. The signals from each electrode pair is provided as signals $P_1(t) \ldots P_N(t)$ to the signal processor 114, which applies these signals to the flow logic 36 to determine the velocity and other parameters of the fluid 102. Variations in the capacitance of the fluid 102 will convect or "ride" along with the fluid flow and therefore represent a characteristic that is directly tied to the flow rate of the fluid 102. It should be appreciated that instead of capacitance, or in addition to capacitance, other electrical characteristics of the fluid may be sensed by the array 108. For example, conductance, resistance, impedance, and the like may similarly be sensed by the array 108.

Figure 8:
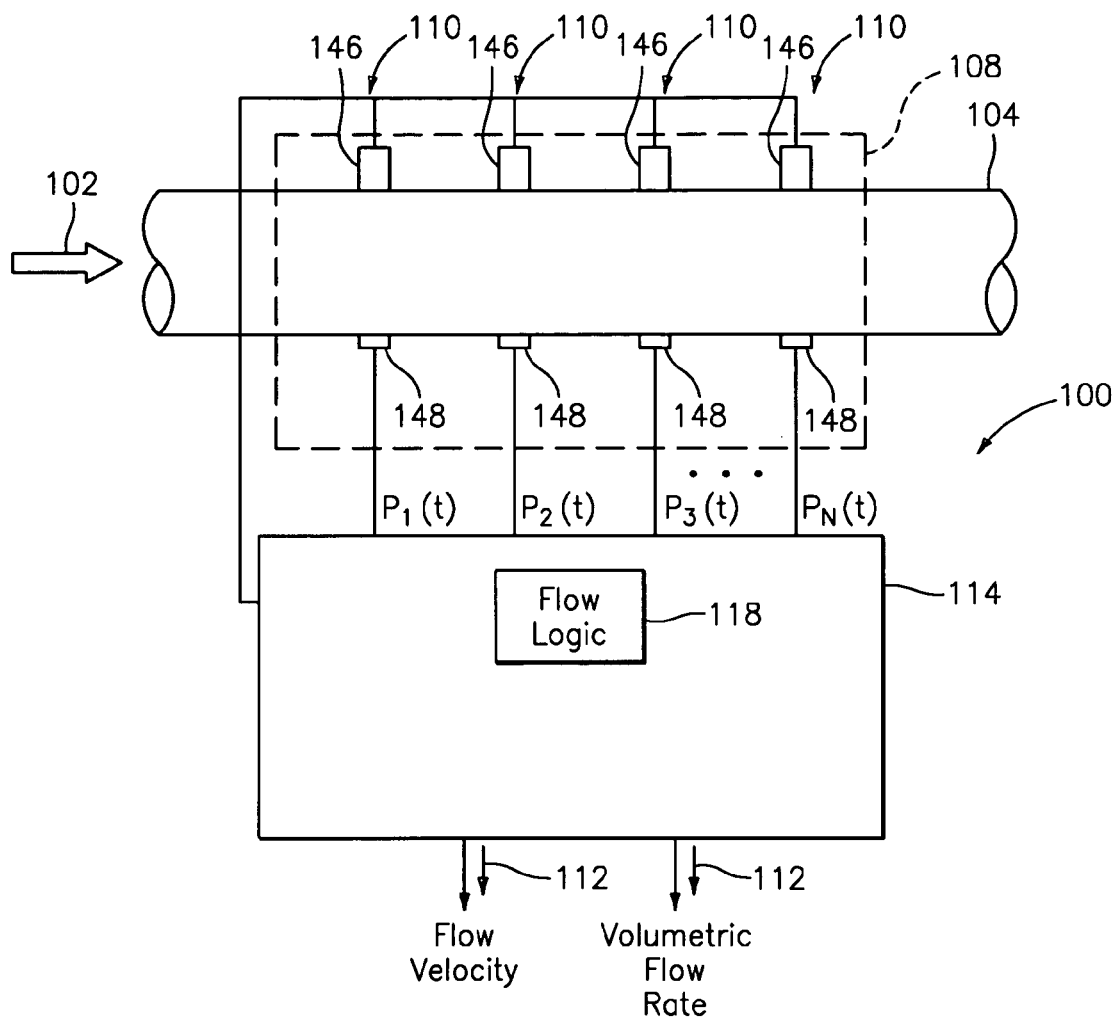
FIG. 8 is a schematic diagram of an apparatus for determining at least one parameter associated with a fluid flowing in a pipe using an array of light transmitters and sensors.
Figure 9:
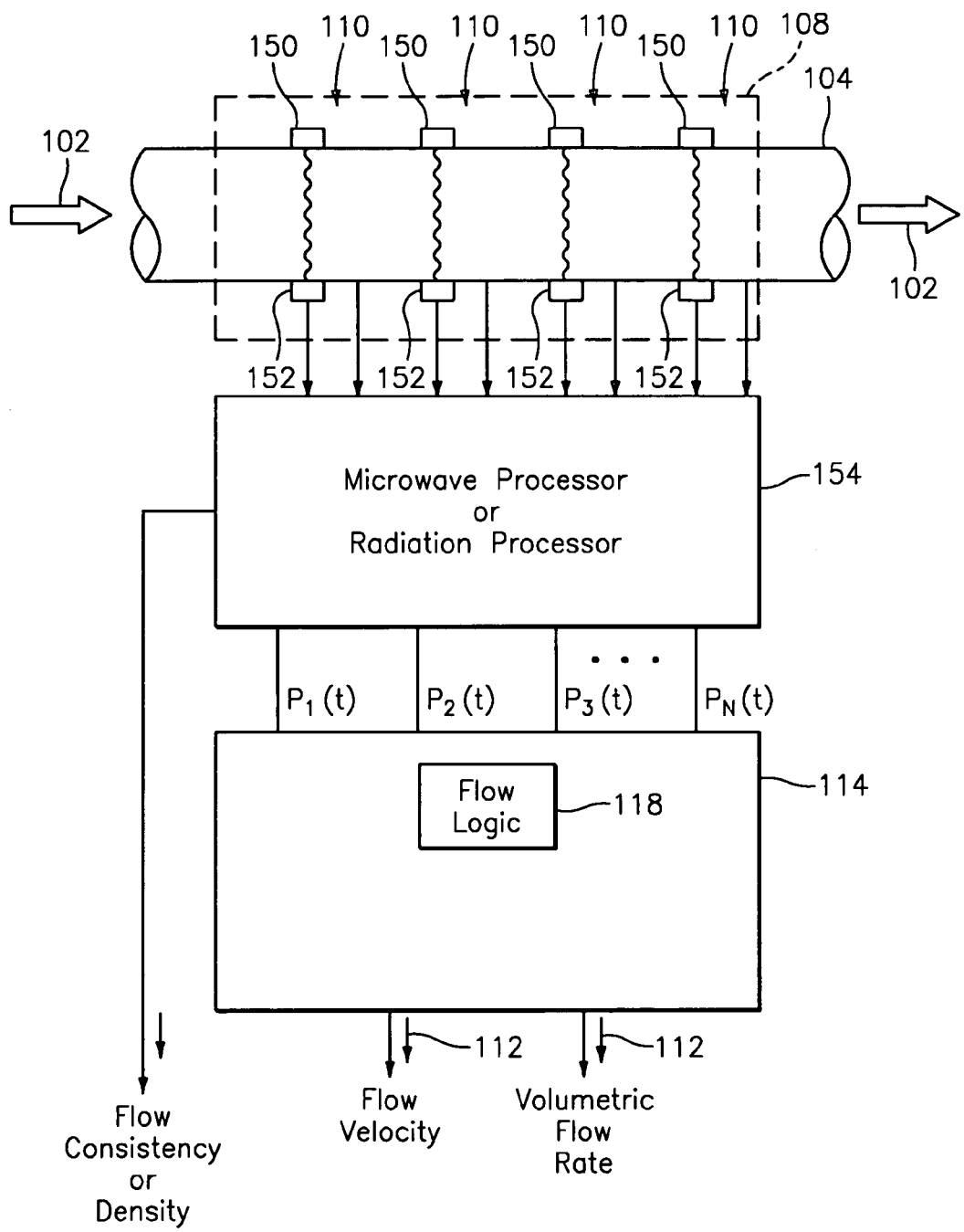
FIG. 9 is a schematic diagram of an apparatus for determining at least one parameter associated with a fluid flowing in a pipe using an array of microwave or radiation transmitters and sensors.

Other examples of stochastic parameters that may be sensed by the array 108 include those that affect one or more of: absorption, attenuation, time delay, and phase delay of energy applied to the mixture 102. FIG. 8 and FIG. 9 depict embodiments in which each sensor 110 includes a transmitter that applies energy to the fluid 102 in the form of electromagnetic or particulate radiation and a sensor that detects the absorption, attenuation, time delay, or phase delay of the energy as it propagates through the fluid 102. In the embodiment of FIG. 8, each transmitter 146 applies energy to the fluid in the form of a light (e.g., laser light) signal, and the sensors 148 (e.g., photodetectors) sense the absorption, attenuation, time delay, or phase delay of the light signal as it passes through the fluid 102. The voltage signals from the sensors 148 are provided as signals $P_1(T) \ldots P_N(T)$ to the signal processor 114, which applies these signals to the flow logic 118 to determine the velocity and other parameters of the fluid 102. Stochastic parameters of the fluid 102 that affect the absorption, attenuation, time delay, and/or phase delay of the light by the fluid will convect or "ride" along with the fluid flow and therefore represent a characteristic that is directly tied to the flow rate of the fluid 102.

In the embodiment of FIG. 9, each transmitter 150 may apply energy in the form of microwave signals, and the sensors 152 may sense the absorption, attenuation, time delay, and/or phase delay of the microwave signals. The transmitters 150 and sensors 152 may be substantially similar to those found in microwave consistency meters, which typically use only one transmitter/sensor pair. An example of a microwave consistency meter that measures the speed or velocity at which a microwave signal propagates through the fluid is manufactured by Toshiba International Corporation of Japan. An example of a microwave consistency meter that measures the time of flight of a microwave signal through the fluid is manufactured by Metso Automation of Finland and sold under the trade name kajaaniMCA™. Another type of consistency meter employs a small gamma source as the transmitter, which is attenuated as it passes through the fluid, wherein the attenuation, which is detected by a scintillation detector (the receiver), is proportional to the changes in consistency. This type of consistency meter is commercially available from Berthold Industrial Systems of Australia.

Referring again to the embodiment of FIG. 9, signals from each sensor 110 in the array 108 can be averaged and used as input to a processor 154 which may be associated with a standard consistency meter and which may determine a consistency of the fluid 102 using the averaged signals. The voltage signals from each sensor 110 may also be provided as signals $P_1(T) \ldots P_N(T)$ to the signal processor 114, which applies these signals to the flow logic 118 to determine the velocity and other parameters of the fluid 102. In this mode, the array 108 detects disturbances due to coherent features that affect the consistency of the fluid 102 as these coherent features convect with the flow past the array 108.

It should be appreciated that each transmitter 150 may apply energy in the form of gamma radiation, and the sensors 152 may sense the absorption of the radiation by the fluid 102. The transmitters 150 and sensors 152 may be substantially similar to those found in gamma (radiation) densitometers, which typically use only one transmitter/sensor pair, but which may also use multiple transmitter/sensor pairs. In this embodiment, signals from each sensor 110 in the array 108 can be averaged and used as input to a processor 154 which may be associated with a standard gamma densitometer and which may determine a consistency of the fluid using the averaged signals. The voltage signals from each sensor 152 may also be provided as signals $P_1(T) \ldots P_N(T)$ to the signal processor 114, which applies these signals to the flow logic 118 to determine the velocity and other parameters of the fluid 102. In this mode, the array detects disturbances due to coherent features that affect the density of the fluid 102 as these coherent features convect with the flow past the array 108.

Diagnostic Logic

Figure 10:
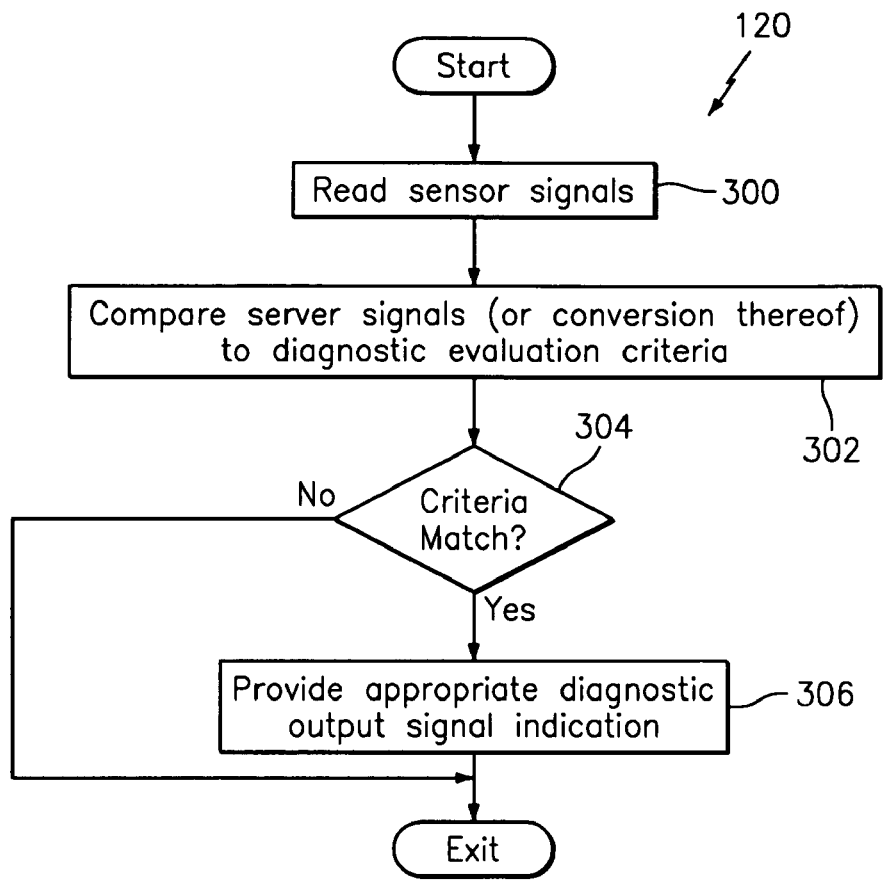
FIG. 10 is a block diagram of a diagnostic logic used in the apparatus of the present invention.

Referring to FIG. 10, a block diagram illustrating the diagnostic logic 120 is shown, wherein the diagnostic logic 120 measures the sensor input signals (or evaluation input signals), which may include one or more of the signals $P_1(t)$, $P_2(t)$, $P_3(t)$, ... $P_N(t)$ and the parameters 112, as shown in operational block 300. The diagnostic logic 120 compares the evaluation input signals to a diagnostic evaluation criteria, as shown in operational block 302, as discussed in further detail hereinafter. The diagnostic logic 120 checks whether there is a match, as shown in operational block 304, and if so, provides a diagnostic signal indicative of the diagnostic condition that has been detected, as shown in operational block 306, wherein the diagnostic logic 120 may also provide information identifying the diagnosed device. Furthermore, the diagnostic signal may also be output as a parameter 112. It should be appreciated that where the evaluation input signal is a parameter 112, as may be output from the flow logic 118, the diagnostic evaluation criteria may be based on a threshold value of the flow signal. For example, the threshold value may be indicative of a maximum or minimum sound speed, mach number, consistency, composition, entrained air, density, mass flow rate, volumetric flow rate, and/or the like. If there is not a criteria match in operational block 304, the diagnostic logic 120 exits.

It should also be appreciated that where the evaluation input signal includes one or more signals $P_1(t)$, $P_2(t)$, $P_3(t)$, ... $P_N(t)$, the diagnostic evaluation criteria may be a threshold (maximum or minimum) signal. Alternatively, the diagnostic evaluation criteria may be based on an acoustic signature, or a convective property (i.e., a property that propagates or convects with the flow). For example, the diagnostic logic 120 may monitor the acoustic signature of any upstream or downstream device (e.g., motor, fan, pump, generator, engine, gear box, belt drive, pulley, hanger, clamp, actuator, valve, meter, or other machinery, equipment or component). Furthermore, it is contemplated that the data from the array 108 may be processed in any domain, including the frequency/spatial domain, the temporal/spatial domain, the temporal/wave-number domain, or the wave-number/frequency (k-ω) domain or other domain, or any of the above. As such, any known array processing technique in any of these or other related domains may be used if desired.

For example, for three signals, the equations in the frequency/spatial domain equation may be given by:

$$P(x,\omega) = Ae^{-ik_r x} + Be^{+ik_l x}, \quad \text{(Eqn. 2)}$$

the temporal/spatial domain may be given by:

$$P(x,t) = (Ae^{-ik_r x} + Be^{+ik_l x})e^{i\omega t}, \quad \text{(Eqn. 3)}$$

and, the k-ω domain (taking the spatial Fourier transform) may be given by:

$$P(k, \omega) = \frac{1}{2\pi} \int_{-\infty}^{+\infty} P(x, \omega) e^{ikx} dx \quad \text{(Eqn. 4)}$$
$$= A(\omega)\delta\left(k - \frac{\omega}{a}\right) + B(\omega)\delta\left(k + \frac{\omega}{a}\right),$$

where k is the wave number, a is the speed of sound of the material, x is the location along the pipe, ω is frequency (in rad/sec, where ω=2πf), and δ is the Dirac delta function, which shows a spatial/temporal mapping of the acoustic field in the k-ω plane.

Moreover, any technique known in the art for using a spatial (or phased) array of sensors to determine the acoustic or convective fields, beam forming, or other signal processing techniques, may be used to provide an input evaluation signal to be compared to the diagnostic evaluation criteria.

Flow Logic

Velocity Processing

Figure 11:
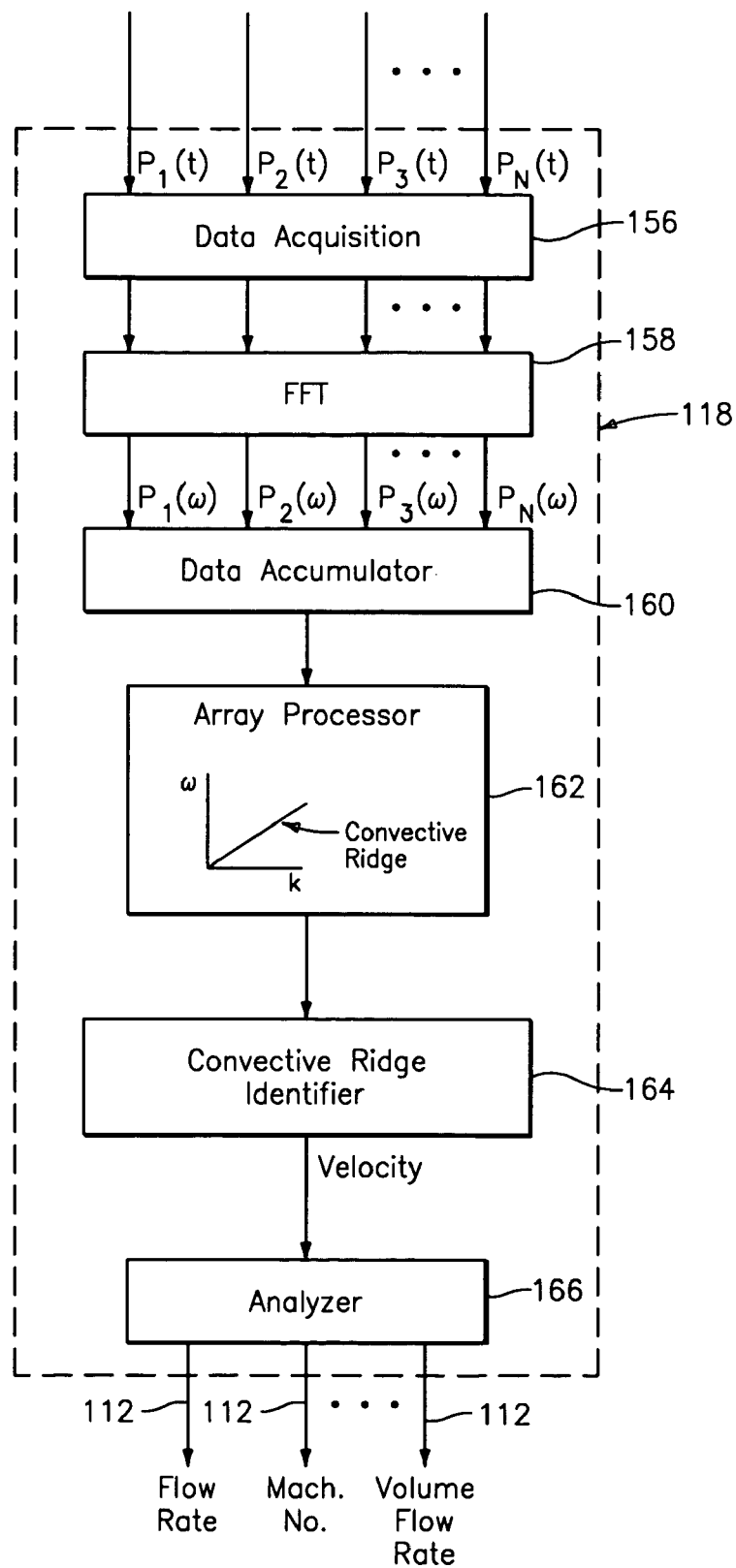
FIG. 11 is a block diagram of a first embodiment of a flow logic used in the apparatus of the present invention.

Referring to FIG. 11, a block diagram illustrating an example of flow logic 118 is shown. As previously described, the array 108 of at least two sensors 110 located at two locations $x_1$, $x_2$ axially along the pipe 104 sense respective stochastic parameter propagating between the sensors 110 within the pipe 104 at their respective locations $x_1 \ldots x_N$. Each sensor 110 provides a signal $P_1(t),P_2(t),P_3(t) \ldots P_N(t)$ indicative of the characteristic at each instant in a series of sampling instants. One will appreciate that the array 108 may include more than two sensors 110 distributed at locations $x_1 \ldots x_N$. The sensors 110 provide the analog time-varying signals $P_1(t),P_2(t),P_3(t) \ldots P_N(t)$ to the signal processor 114, which in turn applies these signals $P_1(t),P_2(t),P_3(t), \ldots P_N(t)$ to the flow logic 118, wherein the flow logic 118 processes the signals $P_1(t),P_2(t),P_3(t), \ldots P_N(t)$ to provide output signals (parameters) 112. The signal processor 114 includes a data acquisition unit 156 (e.g., A/D converter) that converts the analog signals $P_1(t) \ldots P_N(t)$ to respective digital signals and provides the digital signals $P_1(t) \ldots P_N(t)$ to an FFT logic 158. The FFT logic 158 calculates the Fourier transform of the digitized time-based input signals $P_1(t) \ldots P_N(t)$ and provides complex frequency domain (or frequency based) signals $P_1(\omega),P_2(\omega),P_3(\omega), \ldots P_N(\omega)$ indicative of the frequency content of the input signals to a data accumulator 160. It should be appreciated that instead of FFT's, any other technique for obtaining the frequency domain characteristics of the signals $P_1(t)$-$P_N(t)$, may be used. For example, the cross-spectral density and the power spectral density may be used to form a frequency domain transfer functions (or frequency response or ratios) discussed hereinafter. One technique of determining the convection velocity of the stochastic parameter associated with the process flow 102 is by characterizing a convective ridge of the resulting unsteady characteristics associated with the fluid using an array of sensors or other beam forming techniques, similar to that described in U.S. patent application Ser. No. 10/007,736 and U.S. patent application Ser. No. 09/729,994, filed Dec. 4, 2000, now issued into U.S. Pat. No. 6,609,069, all of which are incorporated herein by reference in their entireties.

The data accumulator 160 accumulates the frequency signals $P_1(\omega)$-$P_N(\omega)$ over a sampling interval, and provides the data to an array processor 162, which performs a spatial-temporal (two-dimensional) transform of the sensor data, from the x-t domain to the k-ω domain, and then calculates the power in the k-ω plane, as represented by a k-ω plot. The array processor 162 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by k=2π/λ where λ is the wavelength of a spectral component, and corresponding angular frequencies given by ω=2πv.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length.

Figure 13:
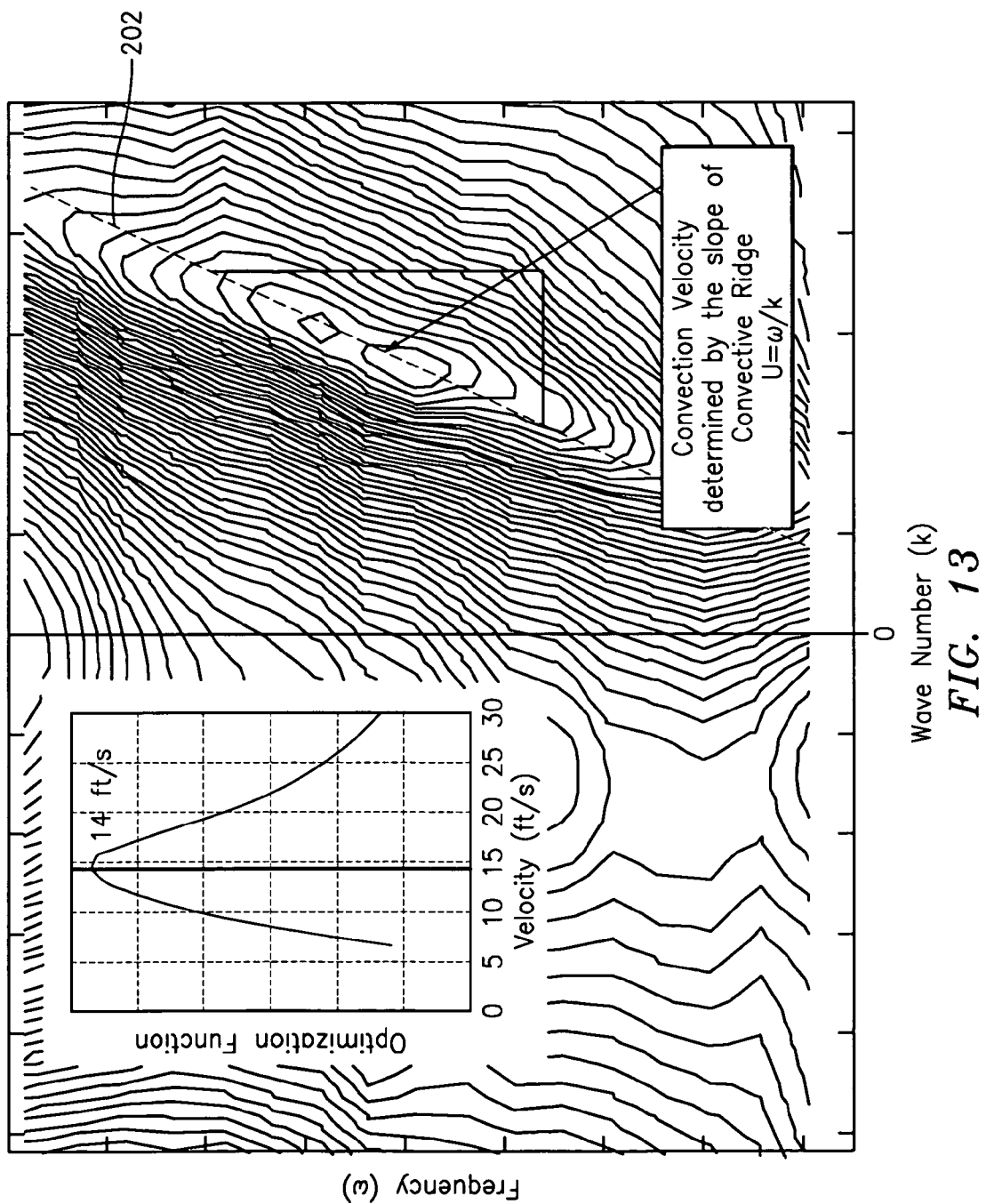
FIG. 13 a k-ω plot of data processed from an apparatus embodying the present invention that illustrates slope of the convective ridge, and a plot of the optimization function of the convective ridge.

It should be appreciated that convective characteristics or parameters have a dispersion relationship that can be approximated by the straight-line equation given by:

$$k=\omega/u, \quad \text{(Eqn. 5)}$$

where u is the convection velocity (flow velocity). Referring to FIG. 13, a plot of k-ω pairs obtained from a spectral analysis of sensor samples associated with convective parameters portrayed so that the energy of the disturbance spectrally corresponding to pairings that might be described as a substantially straight ridge is shown, wherein, in turbulent boundary layer theory, this ridge is called a convective ridge. What is being sensed are not discrete events of the characteristic, but rather a continuum of possibly overlapping events forming a temporally stationary, essentially white process over the frequency range of interest. In other words, the characteristic is distributed over a range of length scales and hence temporal frequencies. To calculate the power in the k-ω plane, as represented by a k-ω plot (see FIG. 13) of either of the signals, the array processor 162 determines the wavelength and so the (spatial) wavenumber k, and also the (temporal) frequency and so the angular frequency ω, of various spectral components of the stochastic parameter. There are numerous algorithms available in the public domain to perform the spatial/temporal decomposition of arrays of sensors 110 and the present invention is not limited to the use of any one of them.

Additionally, the present invention may use temporal and spatial filtering to precondition the signals to effectively filter out the common mode characteristics, Pcommon mode, and other long wavelength (compared to the sensor spacing) characteristics in the pipe 104 by differencing adjacent sensors 110 and retain a substantial portion of the stochastic parameter associated with the flow field and any other short wavelength (compared to the sensor spacing) low frequency stochastic parameters.

Figure 12:
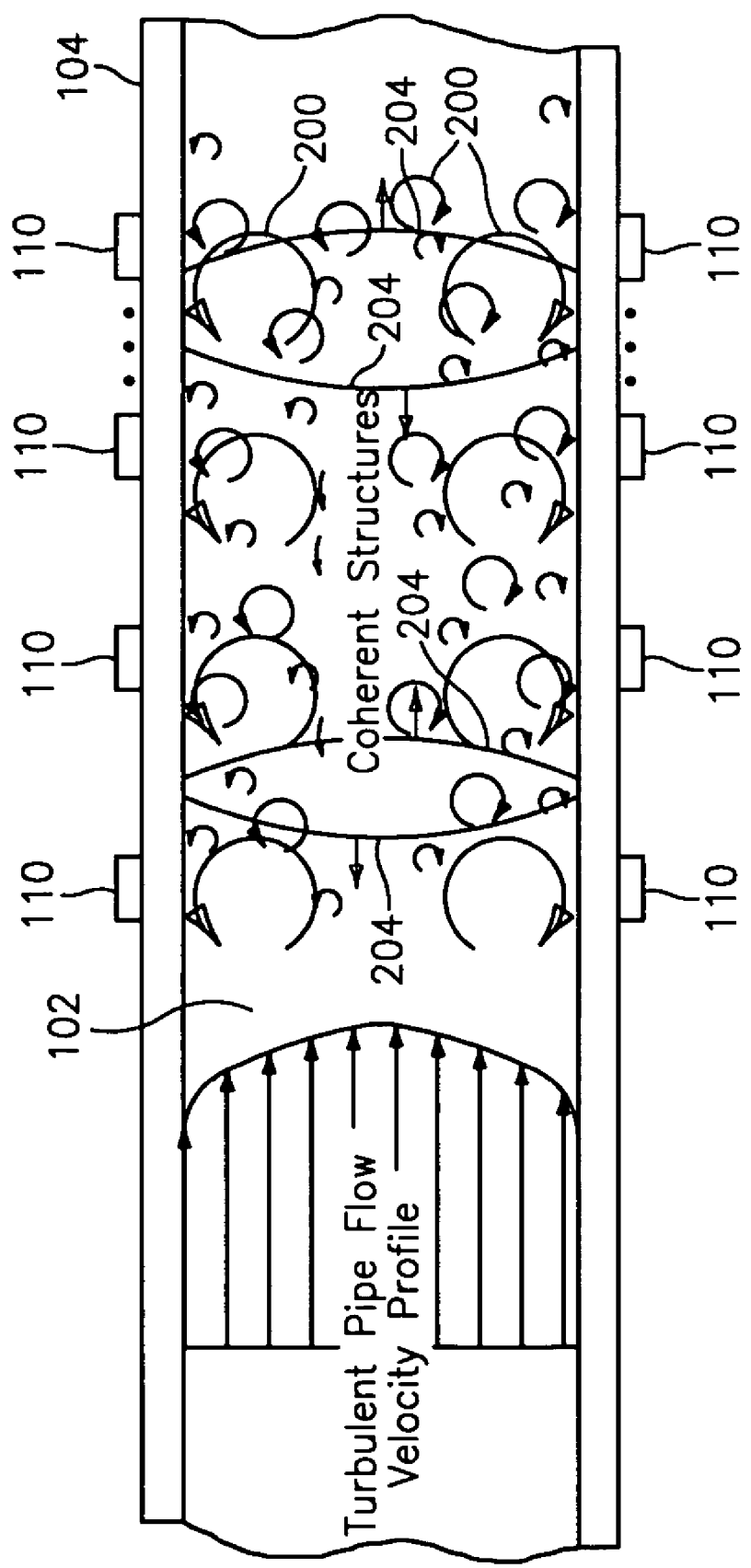
FIG. 12 is a cross-sectional view of a pipe having coherent structures therein.

In the case of suitable turbulent eddies 200 (see FIG. 12) being present, the power in the k-ω plane, as shown in the k-ω plot of FIG. 13, shows a convective ridge 202. The convective ridge 202 represents the concentration of a stochastic parameter that convects with the flow and is a mathematical manifestation of the relationship between the spatial variations and temporal variations described hereinbefore. Such a plot will indicate a tendency for k-ω pairs to appear more or less along a line 202 with some slope, wherein the slope indicates the flow velocity. Once the power in the k-ω plane is determined, a convective ridge identifier 164 uses one or another feature extraction method to determine the location and orientation (slope) of any convective ridge 202 present in the k-ω plane.

In one embodiment, a so-called slant stacking method is used, wherein the slant stacking method is a method in which the accumulated frequency of k-ω pairs in the k-ω plot along different rays emanating from the origin are compared, wherein each different ray is associated with a different trial convection velocity (in that the slope of a ray is assumed to be the flow velocity or correlated to the flow velocity in a known way). The convective ridge identifier 134 provides information about the different trial convection velocities, information referred to generally as convective ridge information, to an analyzer 166, wherein the analyzer 166 examines the convective ridge information including the convective ridge orientation (slope). Assuming the straight-line dispersion relation given by k=ω/u, the analyzer 166 determines the flow velocity, Mach number and/or volumetric flow, which are output as parameters 112. The volumetric flow is determined by multiplying the cross-sectional area of the inside of the pipe with the velocity of the process flow. It should be appreciated that some or all of the functions within the flow logic 118 may be implemented in software (using a microprocessor or computer) and/or firmware, and/or may be implemented using analog and/or digital hardware, having sufficient memory, interfaces, and/or capacity to perform the functions described herein.

Speed of Sound (SOS) Processing

Figure 14:
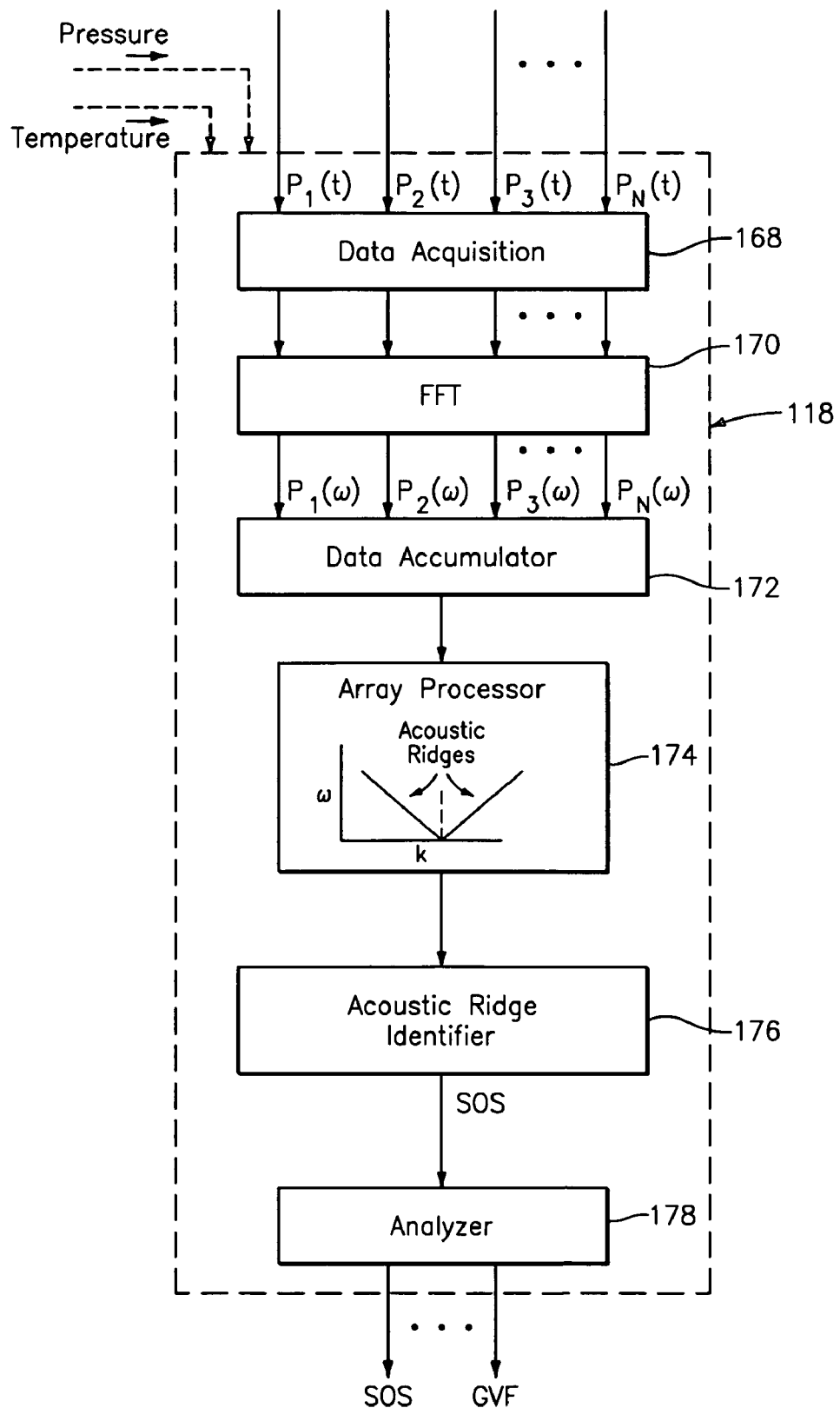
FIG. 14 is a block diagram of a second embodiment of a flow logic used in the apparatus of the present invention.

Referring to FIG. 14, another example of flow logic 118 is shown. It should be appreciated that while the examples of FIG. 11 and FIG. 14 are shown separately, it is contemplated that the flow logic 118 may perform all of the functions described with reference to FIG. 11 and FIG. 14. As previously described, the array 108 of at least two sensors 110 located in at least two locations x1, x2 axially along the pipe 104 sense respective stochastic signals propagating between the sensors 110 within the pipe 104 at their respective locations. Each sensor 110 provides a signal indicating a characteristic associated with the fluid 102 at the location of each sensor 110, at each instant in a series of sampling instants. One will appreciate that the sensor array 108 may include more than two sensors 110 distributed at locations $x_1 \ldots x_N$. The sensors 110 provide analog time-varying signals $P_1(t), P_2(t), P_3(t), \ldots P_N(t)$ to the flow logic 118, wherein the flow logic 118 processes the signals $P_1(t), P_2(t), P_3(t), \ldots P_N(t)$ from the sensors 110 to first provide output signals indicative of the speed of sound propagating through the fluid (process flow) 102, and subsequently, provide output signals such as velocity, Mach number and volumetric flow rate of the process flow 102.

The signal processor 114 receives the signals from the array 108 of sensors 110 and a data acquisition unit 168 digitizes the signals $P_1(t) \ldots P_N(t)$ associated with the acoustic waves 204 propagating through the pipe 104. Similarly to the FFT logic 158 of FIG. 11, an FFT logic 170 calculates the Fourier transform of the selected digitized time-based input signals $P_1(t) \ldots P_N(t)$ and provides complex frequency domain (or frequency based) signals $P_1(\omega), P_2(\omega), P_3(\omega), \ldots P_N(\omega)$ indicative of the frequency content of the input signals to a data accumulator 172. The data accumulator 172 accumulates the frequency signals $P_1(\omega) \ldots P_N(\omega)$ over a sampling interval, and provides the data to an array processor 174, which performs a spatial-temporal (two-dimensional) transform of the sensor data, from the x-t domain to the k-ω domain, and then calculates the power in the k-ω plane, as represented by a k-ω plot. To calculate the power in the k-ω plane, as represented by a k-ω plot (see FIG. 15) of either the signals or the differenced signals, the array processor 174 determines the wavelength and so the (spatial) wavenumber k, and also the (temporal) frequency and so the angular frequency ω, of various of the spectral components of the stochastic parameter. It should be appreciated that there are numerous algorithms available in the public domain to perform the spatial/temporal decomposition of arrays of sensor units 110 and the present invention is not limited to the use of any one in particular.

Figure 15:
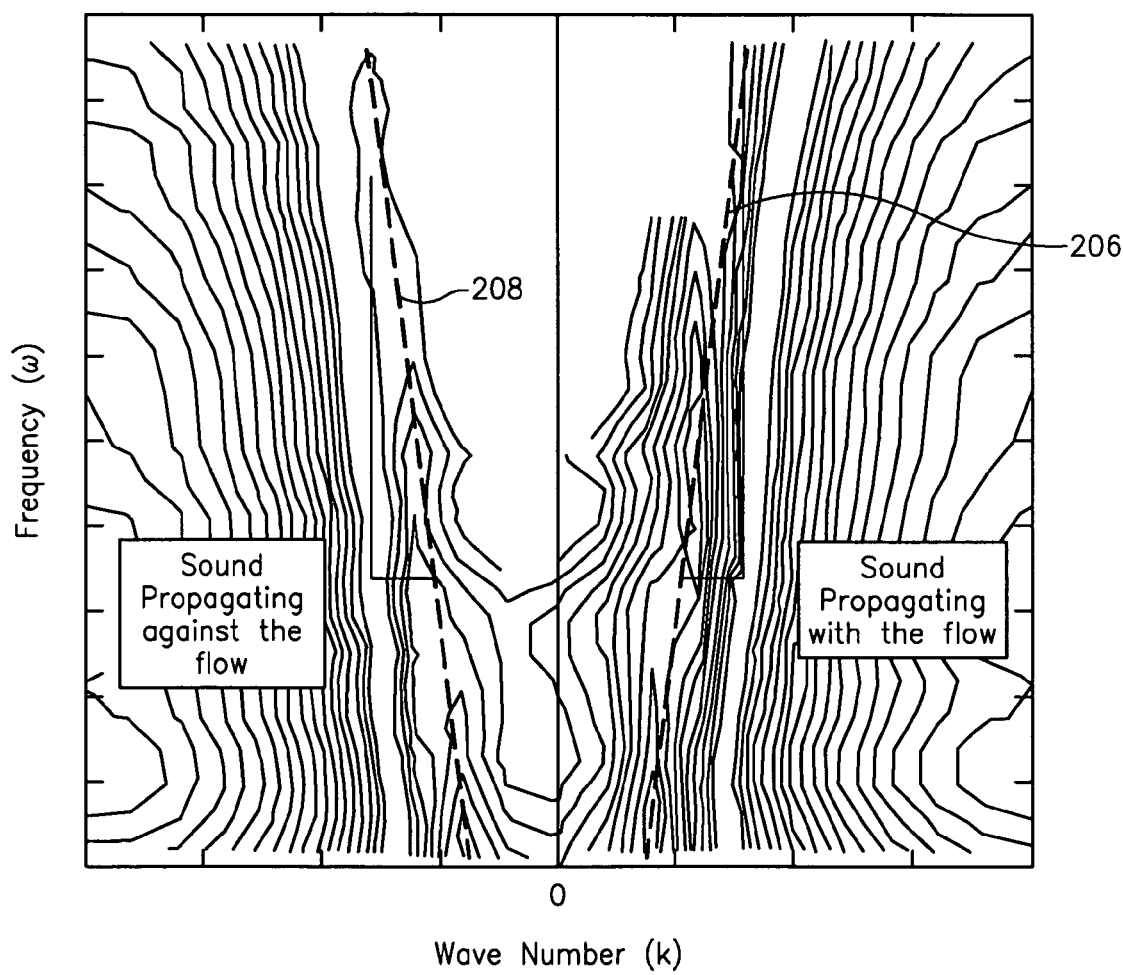
FIG. 15 a k-ω plot of data processed from an apparatus embodying the present invention that illustrates slope of the acoustic ridges.

In the case of suitable acoustic waves 204 being present in both axial directions, the power in the k-ω plane, shown in the k-ω plot of FIG. 15, so determined will exhibit a structure that is called an acoustic ridge 206, 208 in both the left and right planes of the plot, wherein one of the acoustic ridges 206 is indicative of the speed of sound traveling in one axial direction and the other acoustic ridge 208 being indicative of the speed of sound traveling in the other axial direction. The acoustic ridges 206, 208 represent the concentration of a stochastic parameter that propagates through the flow and is a mathematical manifestation of the relationship between the spatial variations and temporal variations described above. Such a plot will indicate a tendency for k-ω pairs to appear more or less along a line 206, 208 with some slope, wherein the slope is indicative of the speed of sound. The power in the k-ω plane so determined is then provided to an acoustic ridge identifier 176, which uses one or another feature extraction method to determine the location and orientation (slope) of any acoustic ridge present in the left and right k-ω plane. The velocity may be determined by using the slope of one of the two acoustic ridges 206, 208 or by averaging the slopes of the acoustic ridges 206, 208. Finally, information including the acoustic ridge orientation (slope) is used by an analyzer 178 to determine the flow parameters relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

Similar to the array processor 162 of FIG. 11, the array processor 174 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$, where λ is the wavelength of a spectral component, and corresponding angular frequencies are given by $\omega=2\pi\nu$. One such technique of determining the speed of sound propagating through the process flow 102 involves using array processing techniques to define an acoustic ridge in the k-ω plane, as shown in FIG. 15. The slope of the acoustic ridge 206, 208 is indicative of the speed of sound propagating through the process flow 102, wherein the speed of sound (SOS) may be determined by applying sonar arraying processing techniques to determine the speed at which the one dimensional acoustic waves propagate past the axial array of sensors 110 distributed along the pipe 104.

The flow logic 118 of the present embodiment measures the speed of sound (SOS) of one-dimensional sound waves propagating through the process flow 102 to determine the gas volume fraction of the process flow 102. It is known that sound propagates through various mediums at various speeds in such fields as SONAR and RADAR fields. Thus, the speed of sound propagating through the pipe 104 and process flow 102 may be determined using any number of known techniques, such as those set forth in U.S. patent application Ser.

No. 09/344,094, filed Jun. 25, 1999, now U.S. Pat. No. 6,354, 147, U.S. patent application Ser. No. 10/795,111, filed Mar. 4, 2004, U.S. patent application Ser. No. 09/997,221, filed Nov. 28, 2001, now U.S. Pat. No. 6,587,798, U.S. patent application Ser. No. 10/007,749, filed Nov. 7, 2001, and U.S. patent application Ser. No. 10/762,410, filed Jan. 21, 2004, each of which are incorporated herein by reference in their entireties. While a sonar-based flow meter is described herein as using an array of sensors 108 to measure the speed of sound of an acoustic wave propagating through the mixture, one should appreciate that any means for measuring the speed of sound of the acoustic wave may be used to determine the entrained gas volume fraction of the mixture/fluid or other characteristics of the flow described hereinbefore.

The analyzer 178 of the flow logic 118 provides output parameters 112 indicative of characteristics of the process flow 102 that are related to the measured speed of sound (SOS) propagating through the process flow 102. For example, to determine the gas volume fraction (or phase fraction), the analyzer 178 assumes a nearly isothermal condition for the process flow 102. As such the gas volume fraction or the void fraction is related to the speed of sound by the following quadratic equation:

$$Ax^2 + Bx + C = 0, \quad \text{(Eqn. 6)}$$

wherein x is the speed of sound, $A = 1 + rg/rl*(K_{eff}/P - 1) - K_{eff}/P$, $B = K_{eff}/P - 2 + rg/rl$; $C = 1 - K_{eff}/rl*a_{meas}\hat{}2$); Rg=gas density, rl=liquid density, $K_{eff}$=effective K (modulus of the liquid and pipewall), P=pressure, and $a_{meas}$=measured speed of sound. Effectively, $$\text{Gas Volume Fraction } (GVF) = (-B + \text{sqrt}(B\hat{}2 - 4*A*C))/(2*A), \quad \text{(Eqn. 7)}$$

Alternatively, the sound speed of a mixture can be related to volumetric phase fraction ($\phi_i$) of the components and the sound speed (a) and densities ($\rho$) of the component through the Wood equation, as given by, $$\frac{1}{\rho_{mix} a_{mix\infty}^2} = \sum_{i=1}^{N} \frac{\phi_i}{\rho_i a_i^2}, \quad \text{(Eqn. 8)}$$

where, $$\rho_{mix} = \sum_{i=1}^{N} \rho_i \phi_i. \quad \text{(Eqn. 9)}$$

As such, the relationship among the infinite domain speed of sound and density of a mixture, the elastic modulus (E), thickness (t), and radius (R) of a vacuum-backed cylindrical conduit and the effective propagation velocity ($a_{eff}$) for one dimensional compression may be given by the following expression:

$$a_{eff} = \frac{1}{\sqrt{1/a_{mix\infty}^2 + \rho_{mix} \frac{2R}{Et}}}, \quad \text{(Eqn. 10)}$$

Figure 16:
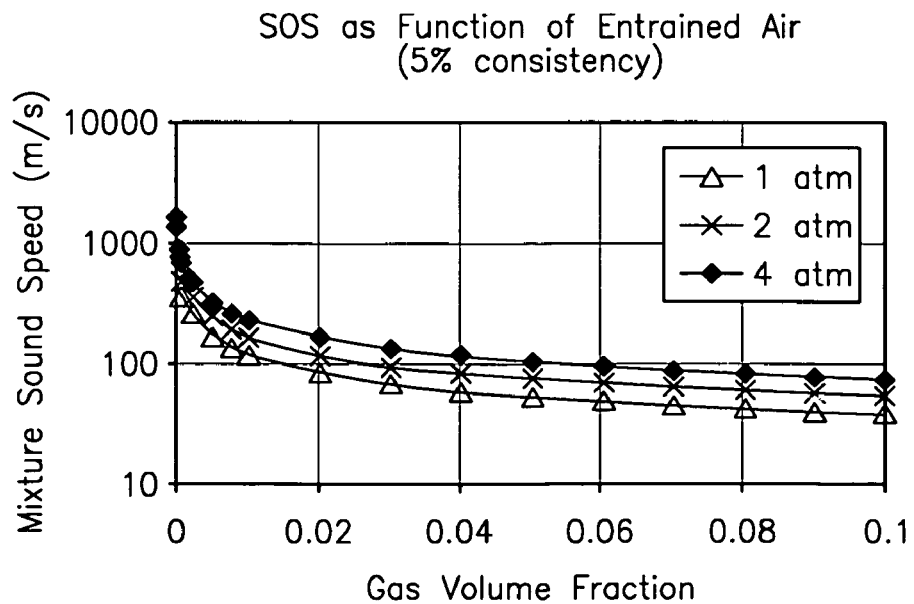
FIG. 16 is a plot of mixture sound speed as a function of gas volume fraction for a 5% consistency slurry over a range of process pressures.

The mixing rule essentially states that the compressibility of a process flow is the volumetrically-weighted average of the compressibilities of the components. For a process flow 102 consisting of a gas/liquid mixture at pressure and temperatures typical of the paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of the volumetric fraction of entrained gas. The effect of process pressure on the relationship between sound speed and entrained air volume fraction is shown in FIG. 16.

As described hereinbefore, the flow logic 118 of the present embodiment includes the ability to accurately determine the average particle size of a particle/air and/or droplet/air mixture within the pipe 104 and/or the air to particle ratio. Provided there is no appreciable slip between the air and the solid coal particle, the propagation of a one dimensional sound wave through multiphase mixtures is influenced by the effective mass and the effective compressibility of the mixture. For an air transport system, the degree to which the no-slip assumption applies is a strong function of particle size and frequency. In the limit of small particles and low frequency, the no-slip assumption is valid. However, as the size of the particles increases and the frequency of the sound waves increase, the non-slip assumption becomes increasing less valid. For a given average particle size, the increase in slip with frequency causes dispersion, or, in other words, the tendency of the sound speed of the mixture to change with frequency. With appropriate calibration the dispersive characteristic of a process flow 102 will provide a measurement of the average particle size, as well as, the air to particle ratio (particle/fluid ratio) of the process flow 102.

In accordance with the present invention the dispersive nature of the system utilizes a first principles model of the interaction between the air and particles. This model may be viewed as being representative of a class of models that seek to account for dispersive effects, although other models could be used to account for dispersive effects without altering the intent of this disclosure (for example, see the paper titled "Viscous Attenuation of Acoustic Waves in Suspensions" by R. L. Gibson, Jr. and M. N. Toksöz), which is incorporated herein by reference in its entirety. The model allows for slip between the local velocity of the continuous fluid phase and that of the particles.

The following relation can be derived for the dispersive behavior of an idealized fluid particle mixture.

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}, \quad \text{(Eqn. 11)}$$

wherein, in the above relation, the fluid SOS, density ($\rho$) and viscosity ($\phi$) are those of the pure phase fluid, $v_p$ is the volume of individual particles and $\rho_p$ is the volumetric phase fraction of the particles in the mixture.

Figure 17:
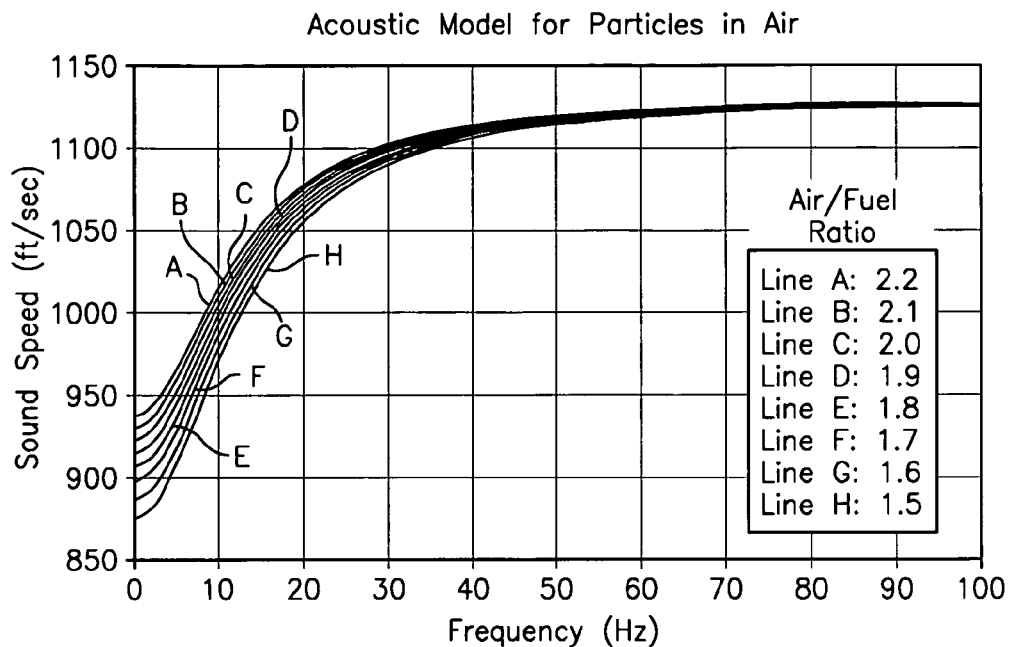
FIG. 17 is a plot of sound speed as a function of frequency for air/particle mixtures with fixed particle size and varying air-to-particle mass ratio.
Figure 18:
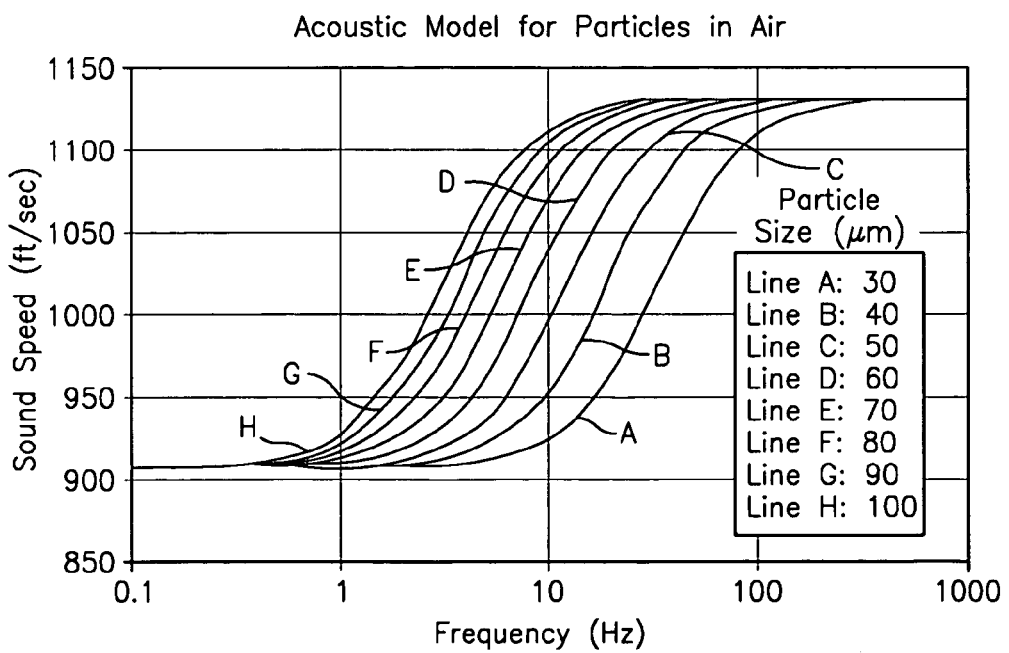
FIG. 18 is a plot of sound speed as a function of frequency for air/particle mixtures with varying particle size where the air-to-particle mass ratio is fixed.

Two parameters of particular interest in steam processes and air-conveyed particles processes are particle size and air-to-fuel mass ratio or steam quality. To this end, it is of interest to examine the dispersive characteristics of the mixture as a function of these two variables. FIG. 17 and FIG. 18 show the dispersive behavior in relations to the speed of sound for coal/air mixtures with parameters typical of those used in pulverized coal deliver systems. In particular FIG. 17 shows the predicted behavior for nominally 50 micrometer size coal in air for a range of air-to-fuel ratios. As shown, the effect of air-to-fuel ratio is well defined in the low frequency limit. However, the effect of the air-to-fuel ratio becomes indistinguishable at higher frequencies, approaching the sound speed of the pure air at high frequencies (above ~100 Hz). Similarly, FIG. 18 shows the predicted behavior for a coal/air mixture with an air-to-fuel ratio of 1.8 with varying particle size. This figure illustrates that particle size has no influence on either the low frequency limit (quasi-steady) sound speed, or on the high frequency limit of the sound speed. However, particle size does appear to have a pronounced effect in the transition region.

It should be appreciated that FIG. 17 and FIG. 18 illustrate an important aspect of the present invention. Namely, that the dispersive properties of dilute mixtures of particles suspended in a continuous liquid, can be broadly classified into three frequency regimes: low frequency range, high frequency range and a transitional frequency range. Although the effect of particle size and air-to-fuel ratio are interrelated, the predominant effect of air-to-fuel ratio is to determine the low frequency limit of the sound speed to be measured and the predominate effect of particle size is to determine the frequency range of the transitional regions. For example, as particle size increases the frequency at which the dispersive properties appear decreases. For typical pulverized coal applications, this transitional region begins at fairly low frequencies, ~2 Hz for 50 micrometer size particles. Thus, given the difficulties measuring sufficiently low frequencies to apply the quasi-steady model and recognizing that the high frequency sound speed contains no direct information on either particle size or air-to-fuel ratio, it becomes apparent that the dispersive characteristics of the coal/air mixture should be utilized to determine particle size and air-to-fuel ratio based on speed of sound measurements.

It should be appreciated that some or all of the functions within the flow logic 118 may be implemented in software (using a microprocessor or computer) and/or firmware, and/or may be implemented using analog and/or digital hardware, having sufficient memory, interfaces, and capacity to perform the functions described herein. Moreover, while FIG. 11 and FIG. 14 depict two different embodiments of the flow logic 118 to measure various parameters of the flow process, the present invention contemplates that the functions of these two embodiments may be performed by a single flow logic 118. It should be further understood that any of the features, characteristics, alternatives or modifications described regarding a particular embodiment herein may also be applied, used, or incorporated with any other embodiment described herein.

It should also be appreciated that the invention may be embodied in the form of a computer or controller implemented processes. The invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

Additionally, while the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. An apparatus for measuring velocity of a fluid passing through a pipe, the apparatus comprising:
    a spatial array of sensors having at least two sensors disposed at different axial locations along the pipe, wherein said sensors provide at least one signal indicative of a stochastic parameter other than unsteady pressure associated with a characteristic of the fluid, said characteristic including at least one of unsteady temperature, density, consistency, transparency, conductivity, capacitance, resistivity, and inductance; and
    a signal processor, wherein said signal processor is configured to receive said at least one signal and determine the velocity of the fluid using said at least one signal.

2. The apparatus of claim 1, wherein said spatial array includes at least one of 3, 4, 5, 6, 7, 8, 9, 10, 11, 12, 13, 14, 15, 16, 17, 18, 19, 20, 21, 22, 23, and 24 sensors.

3. The apparatus of claim 1, wherein said at least two sensors are temperature sensors for measuring the temperature of the fluid at said axial location.

4. The apparatus of claim 1, wherein said at least two sensors are density sensors for measuring the density of the fluid at said axial location.

5. The apparatus of claim 1, wherein said at least two sensors are microwave sensors for measuring the consistency of the fluid at said axial location.

6. The apparatus of claim 1, wherein said at least two sensors are optical sensors for measuring the transparency of the fluid at said axial location.

7. The apparatus of claim 1, wherein said at least two sensors are conductivity sensors for measuring the conductivity of the fluid at said axial location.

8. The apparatus of claim 1, wherein said at least two sensors are capacitance sensors for measuring the capacitance of the fluid at said axial location.

9. The apparatus of claim 1, wherein said at least two sensors are resistivity sensors for measuring the resistivity of the fluid at said axial location.

10. The apparatus of claim 1, wherein said at least two sensors are inductance sensors for measuring the inductance of the fluid at said axial location.

11. The apparatus of claim 1, wherein said sensors are configured to operably associate with at least one of a magnetic flow meter (magmeter), a temperature sensor, a densitometer, a consistency meter, a light meter, a transparency meter, a conductivity meter, a capacitance meter, a resistivity meter and an inductance meter.

12. A method for measuring velocity of a fluid flowing through a pipe, the method comprising:
    providing a spatial array of sensors having at least two sensors disposed at different axial locations along the pipe, wherein at least one sensor in the array is operable to sense a stochastic characteristic other than unsteady pressure of the fluid convecting within the fluid flow and each is operable to produce at least one signal indicative of the stochastic characteristic, which stochastic characteristic is at least one of temperature, density, consistency, transparency, conductivity, capacitance, resistivity, and inductance;

generating at least one signal indicative of the stochastic characteristic convecting with the flow using the array of sensors; and determining a velocity of the fluid flow using the at least one signal indicative of the convecting stochastic characteristic.

13. The method of claim 12, wherein said at least two sensors include at least one of 3, 4, 5, 6, 7, 8, 9, 10, 11, 12, 13, 14, 15, 16, 17, 18, 19, 20, 21, 22, 23, and 24 sensors.

14. The method of claim 12, wherein each sensor in the array generates at least one signal indicative of the stochastic characteristic convecting with the flow, and further comprising the step of determining an average velocity of the fluid flow using the signals from the array of sensors.

15. An apparatus for measuring velocity of a fluid flowing through a pipe, the apparatus comprising:

a spatial array of sensors having at least two sensors disposed at different axial locations along the pipe, wherein at least one sensor in the array is operable to sense a stochastic characteristic other than unsteady pressure of the fluid convecting within the fluid flow and each is operable to produce at least one signal indicative of the stochastic characteristic, which stochastic characteristic is at least one of temperature, density, consistency, transparency, conductivity, capacitance, resistivity, and inductance; and a signal processor operable to receive the at least one signal from each sensor in the spatial array and measure the velocity of the fluid flow within the pipe using the signals indicative of the convecting stochastic characteristic.

16. The apparatus of claim 15, wherein the sensors within the array are temperature sensors, each operable to measure the stochastic temperature of the fluid flow within the pipe at its respective axial location.

17. The apparatus of claim 15, wherein the sensors within the array are density sensors, each operable to measure the stochastic density of the fluid flow within the pipe at its respective axial location.

18. The apparatus of claim 15, wherein the sensors within the array are microwave sensors, each operable to measure the stochastic consistency of the fluid flow within the pipe at its respective axial location.

19. The apparatus of claim 15, wherein the sensors within the array are optical sensors, each operable to measure the stochastic transparency of the fluid flow within the pipe at its respective axial location.

20. The apparatus of claim 15, wherein the sensors within the array are conductivity sensors, each operable to measure the stochastic conductivity of the fluid flow within the pipe at its respective axial location.

21. The apparatus of claim 15, wherein the sensors within the array are capacitance sensors, each operable to measure the stochastic capacitance of the fluid flow within the pipe at its respective axial location.

22. The apparatus of claim 15, wherein the sensors within the array are resistivity sensors, each operable to measure the stochastic resistivity of the fluid flow within the pipe at its respective axial location.

23. The apparatus of claim 15, wherein the sensors within the array are inductance sensors, each operable to measure the stochastic inductance of the fluid flow within the pipe at its respective axial location.

* * * * *

UNITED STATES PATENT AND TRADEMARK OFFICE
CERTIFICATE OF CORRECTION

PATENT NO. : 7,503,227 B2 Page 1 of 1
APPLICATION NO. : 11/487184
DATED : March 17, 2009
INVENTOR(S) : Michael Davis et al.

It is certified that error appears in the above-identified patent and that said Letters Patent is hereby corrected as shown below:

1. In column 18 at line 6, "may" should be --many--.

Signed and Sealed this

Ninth Day of March, 2010

David J. Kappos
*Director of the United States Patent and Trademark Office*